(12) United States Patent
Masumoto et al.

(10) Patent No.: US 10,604,731 B2
(45) Date of Patent: Mar. 31, 2020

(54) CELL ANALYZER, CELL ANALYZER CONTROLLING METHOD, AND PROGRAM

(71) Applicant: Sysmex Corporation, Kobe-shi, Hyogo (JP)

(72) Inventors: Kanako Masumoto, Kobe (JP); Takuya Kubo, Kobe (JP); Shigeki Iwanaga, Kobe (JP); Masaya Okada, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 31 days.

(21) Appl. No.: 15/695,633

(22) Filed: Sep. 5, 2017

(65) Prior Publication Data

US 2017/0362553 A1    Dec. 21, 2017

Related U.S. Application Data

(63) Continuation of application No. PCT/JP2016/055947, filed on Feb. 26, 2016.

(30) Foreign Application Priority Data

Mar. 6, 2015  (JP) ................................ 2015-045320

(51) Int. Cl.
  *C12M 1/34* (2006.01)
  *G06T 7/00* (2017.01)
  (Continued)

(52) U.S. Cl.
  CPC ............... *C12M 1/34* (2013.01); *G01N 21/64* (2013.01); *G01N 21/6428* (2013.01);
  (Continued)

(58) Field of Classification Search
  CPC ............ C12M 1/34; G01N 2021/6432; G01N 2021/6441; G01N 21/64; G01N 21/6428;
  (Continued)

(56) References Cited

U.S. PATENT DOCUMENTS

2010/0216652 A1  8/2010  Eberwine et al.
2011/0002530 A1  1/2011  Zhuang et al.
(Continued)

FOREIGN PATENT DOCUMENTS

CN       101918816 A    12/2010
JP       2010-500563 A   1/2010
(Continued)

OTHER PUBLICATIONS

R. Stevens et al., "Analysis of HER2 Gene Amplification Using an Automated Fluorescence in Situ Hybridization Signal Enumeration System" Journal of Molecular Diagnostics, dated Apr. 2007, pp. 144-150 (Year: 2007).*
(Continued)

*Primary Examiner* — Jennifer Wecker
(74) *Attorney, Agent, or Firm* — Brinks Gilson & Lione

(57) ABSTRACT

Provided is a cell analyzer including: a light source unit configured to apply light to test cells each containing first substances which are bound to first fluorescent dyes and which serve as an index for therapeutic strategy judgement; an image capturing unit configured to capture an image of fluorescence caused by the light; a processing unit configured to process the image obtained by the image capturing unit; and a display unit configured to display a process result obtained by the processing unit, wherein the processing unit obtains a first image by performing an inactivation process of quenching the first fluorescent dyes, an activation process of activating a part of the first fluorescent dyes that have been quenched, and an image capturing process of capturing, by means of the image capturing unit, an image of the fluorescence by applying light from the light source unit to each test cell; extracts bright points based on the first fluorescent dyes on the basis of the first image; classifies the extracted bright points into groups each corresponding to
(Continued)

one first substance, thereby to obtain the number of the first substances in the test cell on the basis of the number of the classified groups; obtains therapy index information serving as an index for therapeutic strategy judgement, on the basis of the obtained number of the first substances; and causes the display unit to display the obtained therapy index information.

22 Claims, 18 Drawing Sheets

(51) Int. Cl.
    *G01N 21/64*     (2006.01)
    *G01N 33/50*     (2006.01)
    *G06K 9/00*     (2006.01)
    *C40B 30/00*     (2006.01)

(52) U.S. Cl.
    CPC ..... *G01N 21/6456* (2013.01); *G01N 33/5005* (2013.01); *G06K 9/00134* (2013.01); *G06K 9/00147* (2013.01); *G06T 7/0012* (2013.01); *G01N 2021/6432* (2013.01); *G01N 2021/6441* (2013.01); *G06T 2207/30072* (2013.01)

(58) Field of Classification Search
    CPC ............ G01N 21/6456; G01N 33/5005; G06T 7/0012; G06T 2207/30072
    See application file for complete search history.

(56) References Cited

U.S. PATENT DOCUMENTS

| | | | |
|---|---|---|---|
| 2013/0027518 | A1 | 1/2013 | MacKay et al. |
| 2016/0281151 | A1* | 9/2016 | Kubo ................... C12Q 1/6841 |

FOREIGN PATENT DOCUMENTS

| | | | |
|---|---|---|---|
| JP | 2011-508214 A | 3/2011 | |
| JP | 2012-103077 A | 5/2012 | |
| JP | 5416582 B | 2/2014 | |
| JP | 2014-052746 A | 3/2014 | |
| WO | 2008/091296 A2 | 7/2008 | |
| WO | WO 2009/085218 A1 | 7/2009 | |

OTHER PUBLICATIONS

Rust et al., "Sub-diffraction-limit imaging by stochastic optical reconstruction microscopy (STORM)" Brief Communications, Nature Methods | Advanced Online Publication, published online on Aug. 9, 2006, pp. 1-3.
HER2 Testing, including partial English Translation, dated Sep. 2009, pp. 1-30.
Yoshiro Oikawa, "The Technologies and the Applications of Super Resolution Microscopy", MICROSCOPY, vol. 47, No. 4, 2012, pp. 1-11.
R. Stevens et al., "Analysis of HER2 Gene Amplification Using an Automated Fluorescence in Situ Hybridization Signal Enumeration System" Journal of Molecular Diagnostics, dated Apr. 2007, pp. 144-150, XP55493561, Retrieved from the Internet on Jul. 18, 2018 from URL: <https://www.sciencedirect.com/science/article/pii/S1525157810603741/pdfft?md5=c9f299c2711eefec3263071c00f01032&pid=1-s2.0-S1525157810603741-main.pdf>.
Theodosiou et al., "Evaluation of FISH image analysis systems on assessing HER2 amplification in breast carcinoma cases" Breast, Edinburgh, GB, vol. 17, No. 1, dated Feb. 2008, pp. 80-84, XP022478717.
Gabor Pajor et al., "State-of-the-art FISHing: Automated analysis of cytogenetic aberrations in interphase nuclei" Cytometry, Part A, vol. 81A, No. 8, dated Jun. 13, 2012, pp. 649-663, XP055324200, US.
Rossi, A. et al, Super-resolution imaging of aquaporin-4 orthogonal arrays of particles in cell membranes,Journal of Cell Science, The Company of Biologists Ltd, Sep. 15, 2012—vol. 125/No. 18, pp. 4405-4412; Cited in the Japanese office action dated Mar. 26, 2019 in a counterpart Japanese patent application.
Betzig, E. et al., Imaging Intracellular Fluorescent Proteins at Nanometer Resolution, Science, United States, Aug. 10, 2006, American Association for the Advancement of Science, vol. 313, pp. 1642-1645; Cited in the Japanese office action dated Mar. 26, 2019 in a counterpart Japanese patent application.
Rocha, S.et al., Palm, Superresolution Fluorescence Microscopy Circumventing the Diffraction Limit of Light, to Explore Minute Structures of Cells, Microscopy, Japanese society of Microscopy, Japan, Dec. 30, 2014, vol. 49/ No. 3,pp. 205-210; Cited in the Japanese office action dated Mar. 26, 2019 in a counterpart Japanese patent application.
Dani, A. et al.,Superresolution Imaging of Chemical Synapses in the Brain,Neuron, United States, Dec. 9, 2010, Elsevier Inc., vol. 68,pp. 343-356; Cited in the Japanese office action dated Mar. 26, 2019 in a counterpart Japanese patent application.
Sugawara et al., A super-resolution fluorescence microscope, Drug Delivery System, Japan DDS, Japan, Sep. 25, 2014, vol. 29/No. 4,pp. 354-356; Cited in the Japanese office action dated Mar. 26, 2019 in a counterpart Japanese patent application.
Loschberger, A. et al., Super-resolution imaging visualizes the eightfold symmetry of gp210 proteins around the nuclear pore complex and resolves the central channel with nanometer resolution, Journal of Cell Science, The Company of Biologists Ltd, Feb. 1, 2012, vol. 125/No. 3, pp. 570-575; Cited in the Japanese office action dated Mar. 26, 2019 in a counterpart Japanese patent application.
The Japanese Office Action dated Mar. 26, 2019 in a conterpart Japanese patent application No. 2015-045320.
The Chinese Office Action dated May 29, 2019 in a counterpart Chinese patent application No. 201680014482.3
J. Macqueen, "Some Methods for Classificatioin and Analysis of Multivariate Observations", Proceedings of the Fifth Berkeley Symposium on Mathematical Statistics and Probability, vol. 1, Statistics, University of California Press, Berkeley, California, 1967, pp. 281-297; Attached to the Chinese office action dated Dec. 26, 2019 in a counterpart Chinese patent application.
"Supplementary Methods", https://media.nature.com/original/nature-assets/nmeth/journal/v3/n10/extref/nmeth929-S4.pdf; Attached to the Chinese office action dated Dec. 26, 2019 in a counterpart Chinese patent application.
The Chinese Office Action dated Dec. 26, 2019 in a counterpart Chinese patent application No. 201680014482.3.

\* cited by examiner

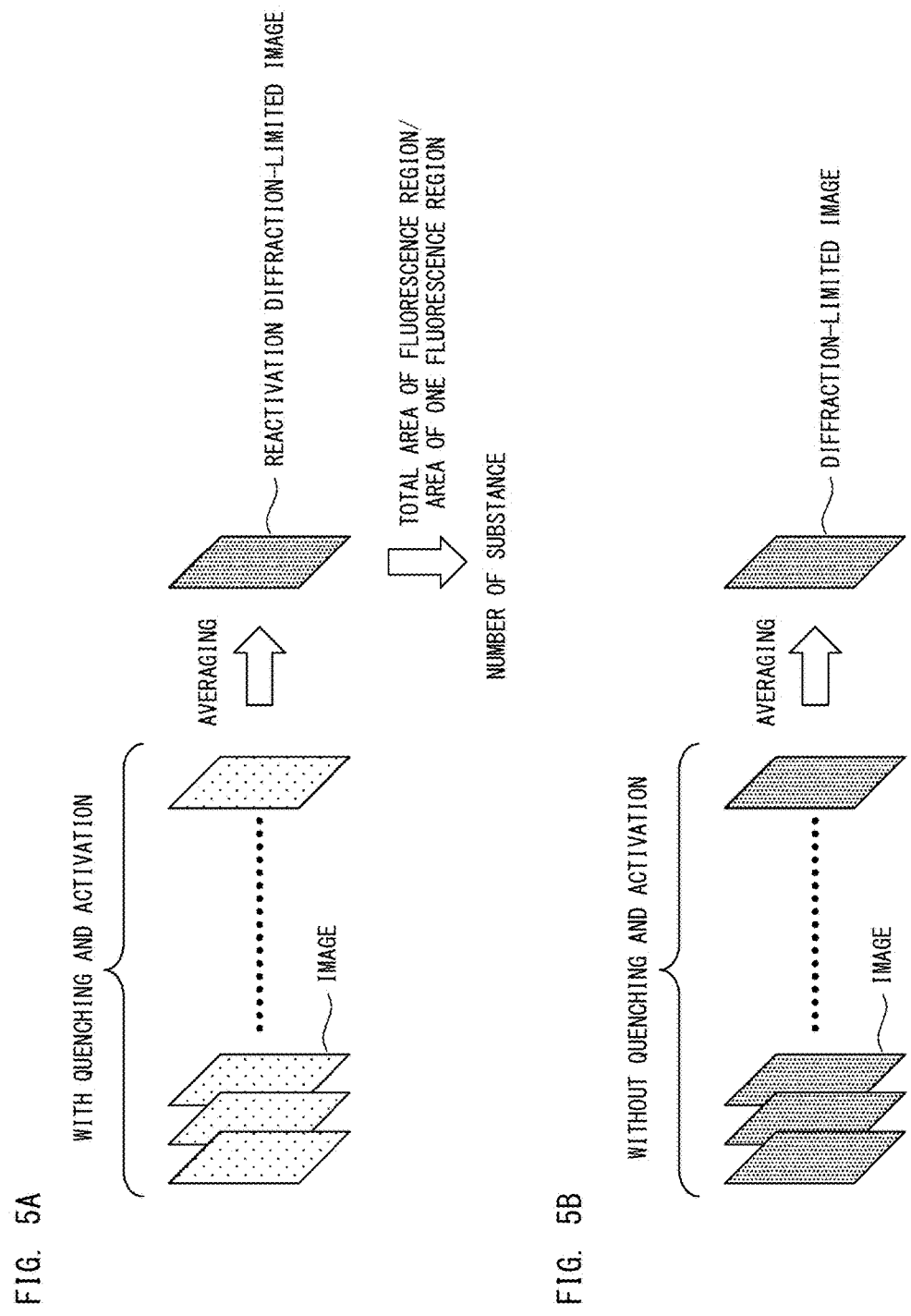

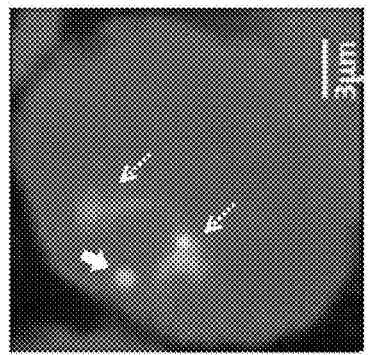
FIG. 8A  EXAMPLE 1
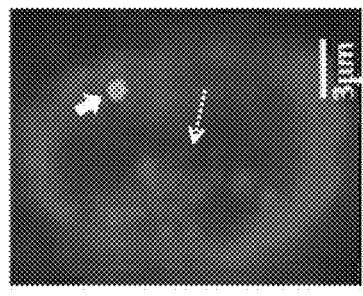
FIG. 8B  EXAMPLE 1
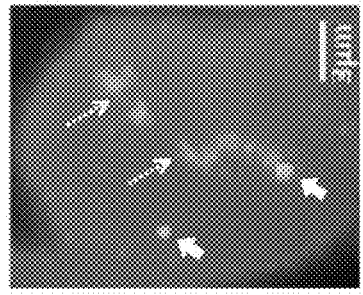
FIG. 8C  EXAMPLE 1
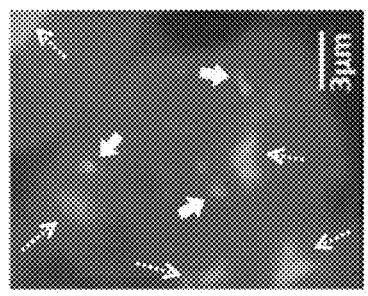
FIG. 8D  EXAMPLE 1

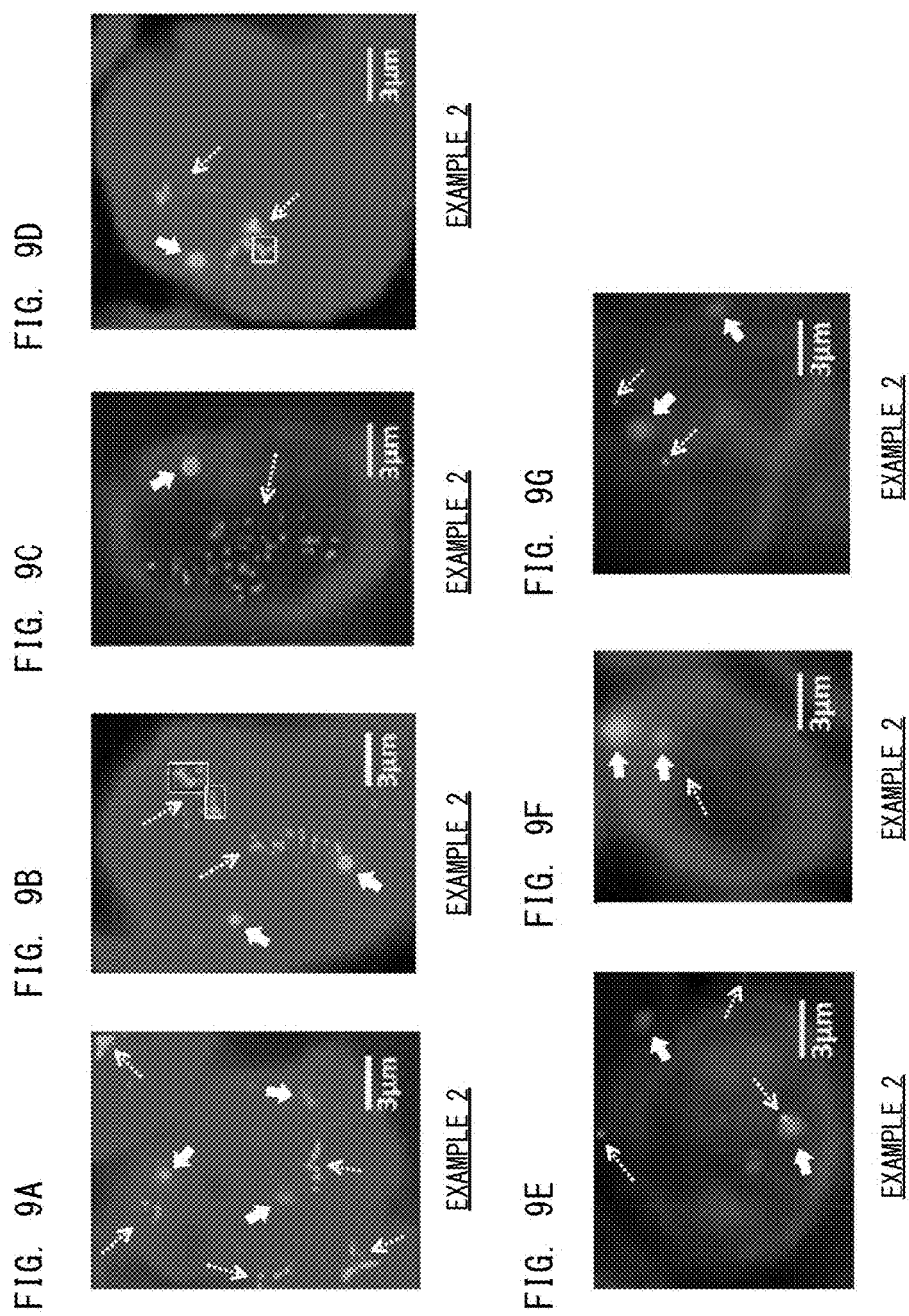

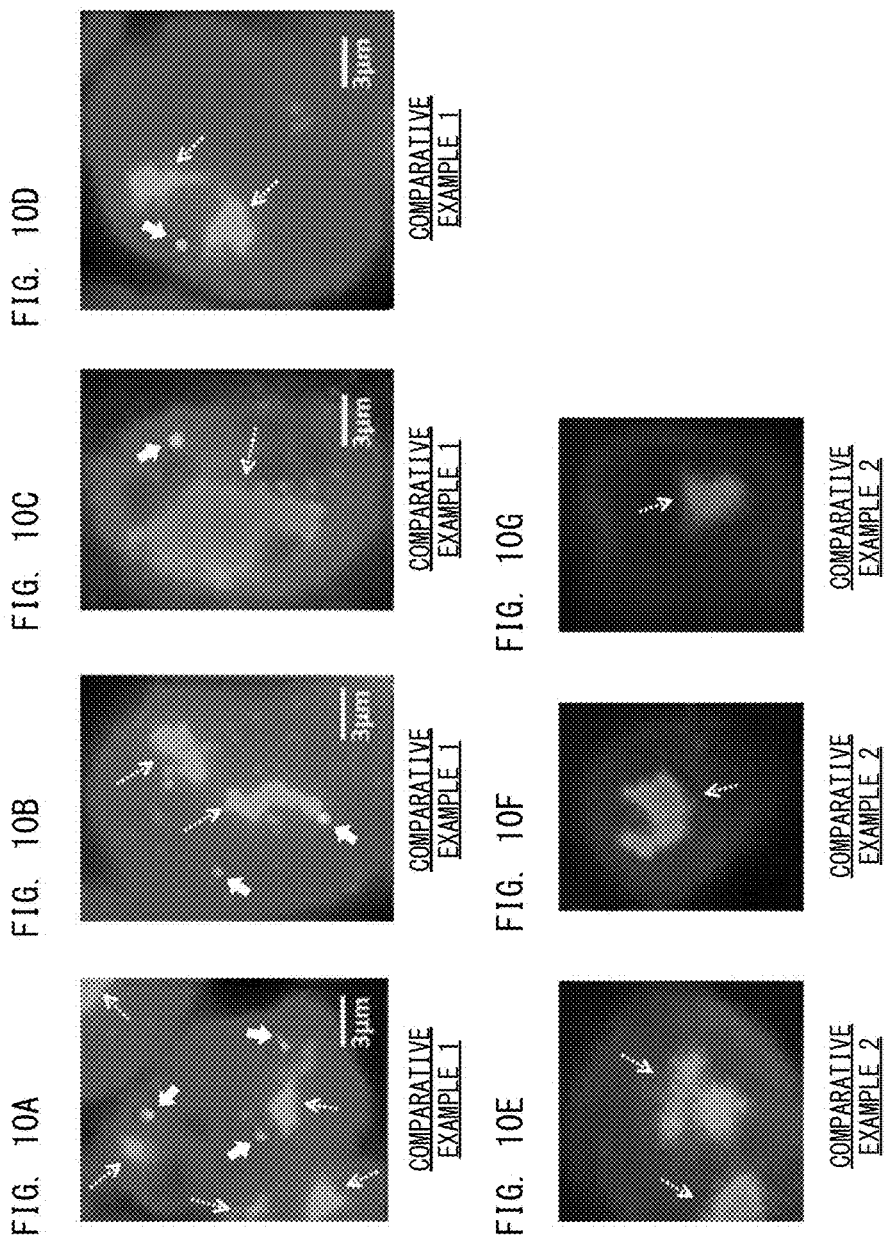

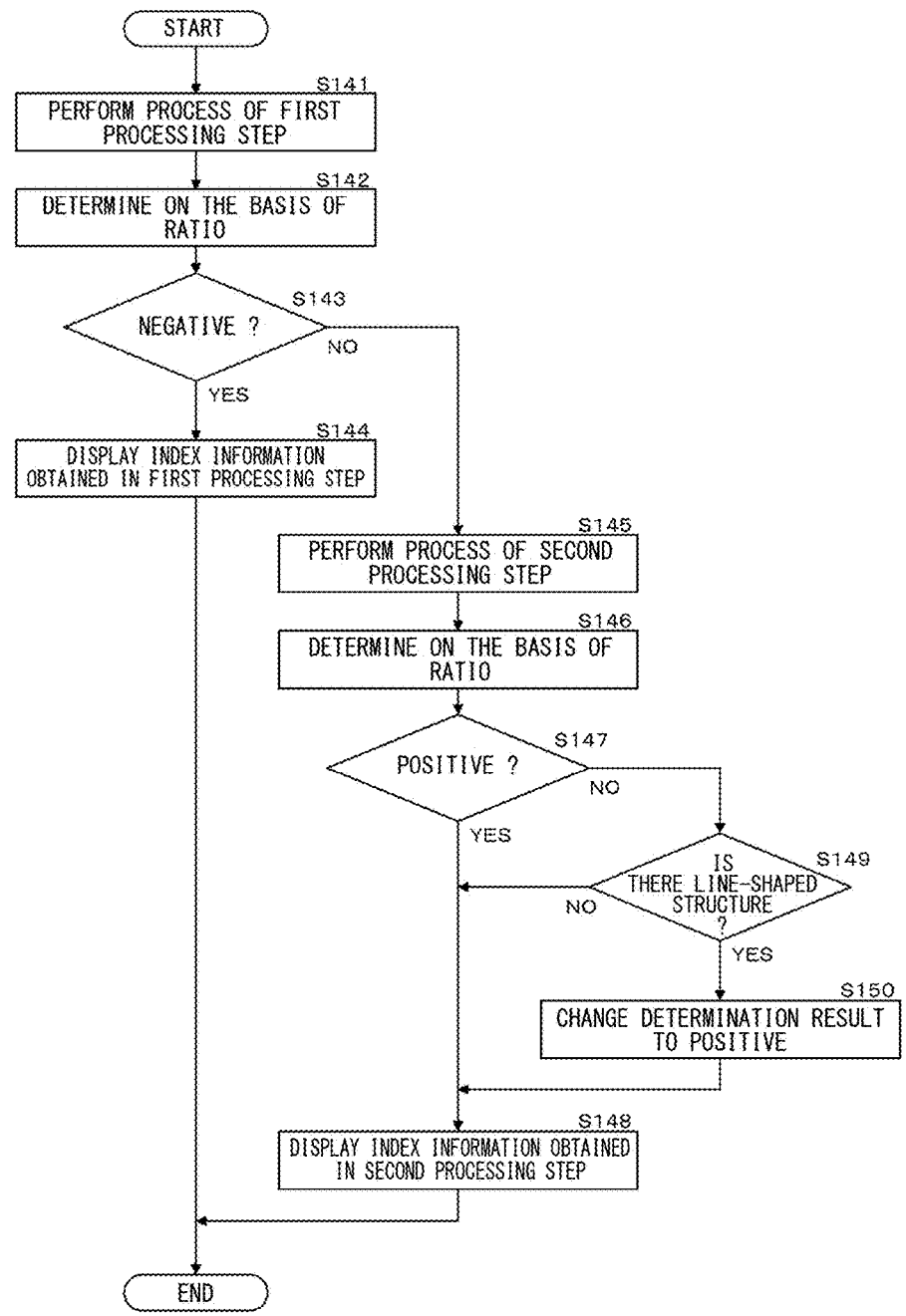

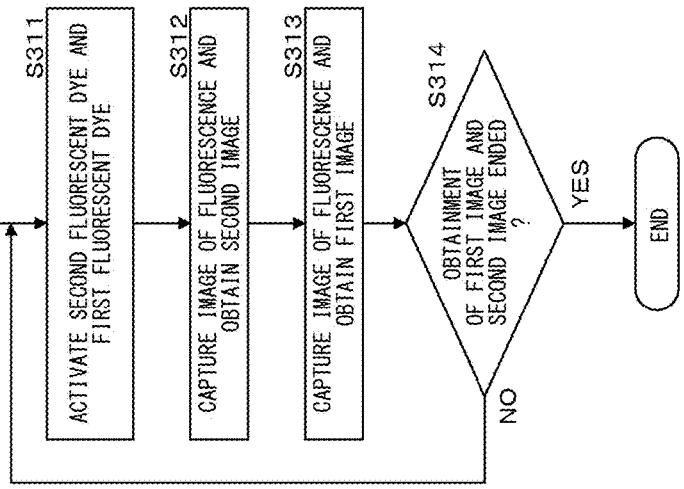
FIG. 15B   IMAGE OBTAINING PROCESS
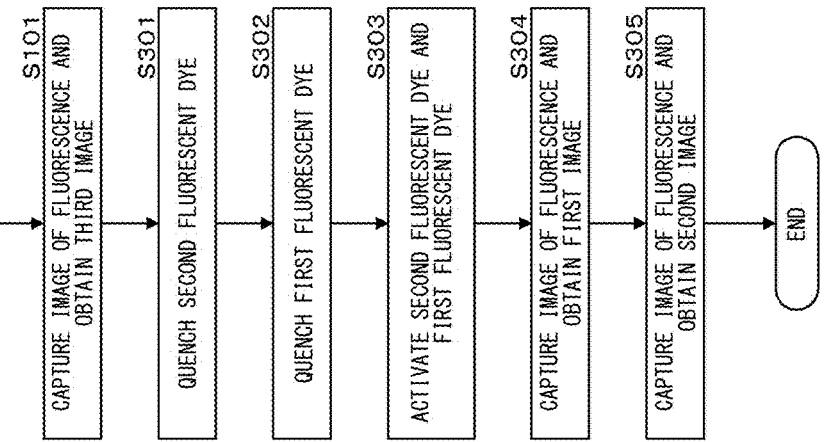
FIG. 15A   IMAGE OBTAINING PROCESS

CELL ANALYZER, CELL ANALYZER CONTROLLING METHOD, AND PROGRAM

RELATED APPLICATIONS

This application is a continuation of International Application PCT/JP2016/055947 filed on Feb. 26, 2016, which claims benefit of Japanese patent application JP 2015-045320 filed on Mar. 6, 2015, both of which are incorporated herein by reference in their entireties.

BACKGROUND OF THE INVENTION

1. Field of the Invention

The present invention relates to a cell analyzer, a cell analyzer controlling method, and a program to be executed by a computer of a cell analyzer.

2. Description of the Related Art

In certain diseases, specific genes, specific proteins, and the like are involved in the progress of disease conditions. To confirm the presence and the state of a specific substance with regard to cells collected from a subject is very useful when making determination of diagnosis and a therapeutic strategy for such a disease.

For example, in the case of breast cancer, HER-2 gene which is a prognostic factor is amplified in accordance with progress of the disease condition. In Japanese Laid-Open Patent Publication No. 2012-103077, amplification of HER-2 gene is analyzed by use of a FISH method. Specifically, a nucleic acid probe (HER-2 probe) that binds to DNA of HER-2 gene and a nucleic acid probe (CEP17 probe) that binds to the centromere region of chromosome 17 (CEP17) are labeled with different kinds of fluorescent dyes, respectively, and fluorescence that occurs from each probe in one cell is counted. Then, when the ratio of the number of fluorescence from HER-2 gene relative to the number of fluorescence from CEP17 is higher than or equal to a predetermined value, amplification of HER-2 gene is determined as positive, and when the ratio is less than the predetermined value, amplification of HER-2 gene is determined as negative.

In the above diagnostic approach, for diagnosis, an image indicating the distribution state of fluorescence is provided to a doctor or the like, for example. The doctor or the like is required to perform complicated work such as making determination on the disease condition while referring to the provided image. In addition, in the diagnostic approach above, the provided image is confirmed through visual observation to determine the disease condition. Thus, the doctor or the like is required to be well skilled in the determination, and the diagnoses could vary depending on the person who makes the determination.

SUMMARY OF THE INVENTION

The scope of the present invention is defined solely by the appended claims, and is not affected to any degree by the statements within this summary.

A cell analyzer according to a first mode of the present invention includes: a light source unit configured to apply light to test cells each containing first substances which are bound to first fluorescent dyes and which serve as an index for therapeutic strategy judgement; an image capturing unit configured to capture an image of fluorescence caused by the light; a processing unit configured to process the image obtained by the image capturing unit; and a display unit configured to display a process result obtained by the processing unit. The processing unit obtains a first image by performing an inactivation process of quenching the first fluorescent dyes, an activation process of activating a part of the first fluorescent dyes that have been quenched, and an image capturing process of capturing, by means of the image capturing unit, an image of the fluorescence by applying light from the light source unit to each test cell; extracts bright points based on the first fluorescent dyes on the basis of the first image; classifies the extracted bright points into groups each corresponding to one first substance, thereby to obtain the number of the first substances in the test cell on the basis of the number of the classified groups; obtains therapy index information serving as an index for therapeutic strategy judgement, on the basis of the obtained number of the first substances; and causes the display unit to display the obtained therapy index information.

A second mode of the present invention relates to a cell analyzer controlling method. The cell analyzer controlling method according to this mode includes: obtaining a first image by performing an inactivation process of quenching first fluorescent dyes bound to first substances which are contained in a test cell and which serve as an index for therapeutic strategy judgement, an activation process of activating a part of the first fluorescent dyes that have been quenched, and an image capturing process of capturing an image of fluorescence by applying light to the test cell; extracting bright points based on the first fluorescent dyes on the basis of the first image; classifying the extracted bright points into groups each corresponding to one first substance, thereby to obtain the number of the first substances in the test cell on the basis of the number of the classified groups; obtaining therapy index information serving as an index for therapeutic strategy judgement, on the basis of the obtained number of the first substances; and displaying the obtained therapy index information.

A non-transitory computer-readable computer medium storing a program according to a third mode of the present invention is a non-transitory computer-readable computer medium storing a program for causing a computer of a cell analyzer to perform operations, the cell analyzer being provided with a light source unit configured to apply light to test cells each containing first substances which are bound to first fluorescent dyes and which serve as an index for therapeutic strategy judgement, an image capturing unit configured to capture an image of fluorescence caused by the light, and a display unit, the operations including: obtaining a first image by performing an inactivation process of quenching the first fluorescent dyes, an activation process of activating a part of the first fluorescent dyes that have been quenched, and an image capturing process of capturing, by means of the image capturing unit, an image of the fluorescence by applying light from the light source unit to each test cell, extracting bright points based on the first fluorescent dyes on the basis of the first image; classifying the extracted bright points into groups each corresponding to one first substance, thereby to obtain the number of the first substances in the test cell on the basis of the number of the classified groups; obtaining therapy index information serving as an index for therapeutic strategy judgement, on the basis of the obtained number of the first substances; and causing the display unit to display the obtained therapy index information.

BRIEF DESCRIPTION OF THE DRAWINGS

FIG. 5A is a diagram describing a procedure for obtaining a reactivation diffraction-limited image and the number of substances according to Embodiment 1;

FIG. 5B is a diagram describing a procedure of obtaining a diffraction-limited image according to Embodiment 1;

FIG. 8A shows a positive reference image obtained in the first processing step according to Embodiment 1;

FIG. 8B shows a positive reference image obtained in the first processing step according to Embodiment 1;

FIG. 8C shows a positive reference image obtained in the first processing step according to Embodiment 1;

FIG. 8D shows a positive reference image obtained in the first processing step according to Embodiment 1;

FIG. 9A shows a positive reference image obtained in the second processing step according to Embodiment 1;

FIG. 9B shows a positive reference image obtained in the second processing step according to Embodiment 1;

FIG. 9C shows a positive reference image obtained in the second processing step according to Embodiment 1;

FIG. 9D shows a positive reference image obtained in the second processing step according to Embodiment 1;

FIG. 9E shows a negative reference image obtained in the second processing step according to Embodiment 1;

FIG. 9F shows a negative reference image obtained in the second processing step according to Embodiment 1;

FIG. 9G shows a negative reference image obtained in the second processing step according to Embodiment 1;

FIG. 10A shows a positive reference image obtained in Comparative Example 1;

FIG. 10B shows a positive reference image obtained in Comparative Example 1;

FIG. 10C shows a positive reference image obtained in Comparative Example 1;

FIG. 10D shows a positive reference image obtained in Comparative Example 1;

FIG. 10E shows a positive reference image obtained in Comparative Example 2;

FIG. 10F shows a positive reference image obtained in Comparative Example 2;

FIG. 10G shows a positive reference image obtained in Comparative Example 2;

FIG. 11 is a flow chart showing a display process according to Embodiment 1;

FIG. 15A is a flow chart showing an image obtaining process in a first processing step according to Modification of Embodiment 2;

FIG. 15B is a flow chart showing an image obtaining process in a second processing step according to Modification of Embodiment 2;

DETAILED DESCRIPTION OF THE PREFERRED EMBODIMENTS

The embodiments below are obtained by applying the present invention to a cell analyzer that obtains information regarding breast cancer.

"Therapy index information" displayed by a cell analyzer is information that serves as an index used by a doctor or the like when deciding a therapeutic strategy such as administration, surgery, or follow up. In the embodiments below, as one example of the therapy index information, the number of HER-2 genes, which is one of prognostic factors for breast cancer, is counted as the number of first substances, and a determination result regarding the ratio between the counted value and the number of CEP17s is obtained and displayed as the therapy index information. On the basis of this therapy index information, the doctor or the like can confirm the state of HER-2 gene amplification. This enables, for example, determination of an administration strategy as to whether Herceptin (registered trade mark), whose generic name is trastuzumab, and which is a molecular target drug whose specific target is HER-2 gene, is to be used in a breast cancer therapy for the patient. It should be noted that what is displayed by the cell analyzer is not limited to the therapy index information described above. The counted value of a disease marker which is the first substances, the ratio between the first substances and second substances, or the like may be outputted as "therapy index information" which serves as an index when the progress state of a disease relevant to the disease marker is to be determined.

1. Embodiment 1

Figure 1:
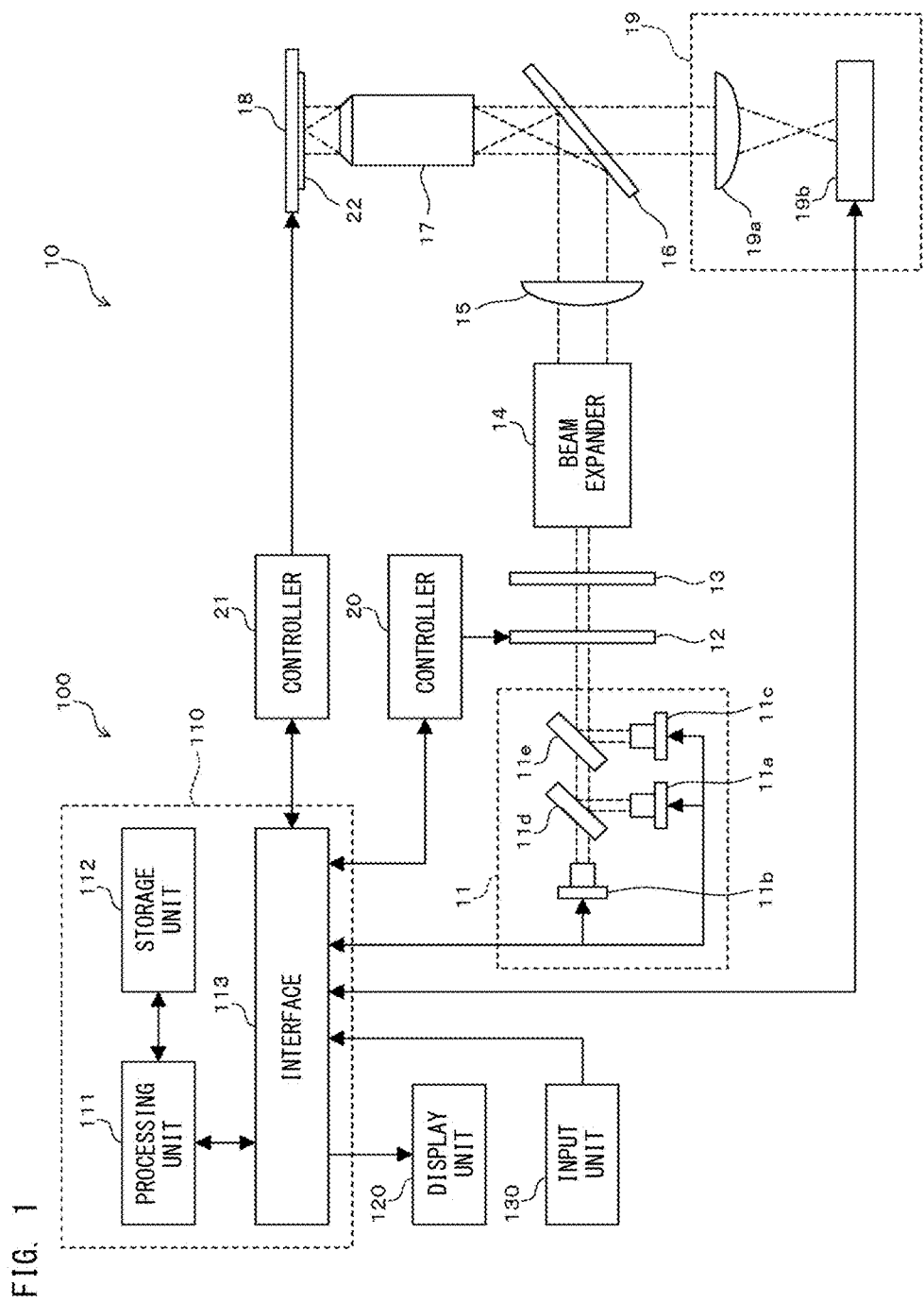
FIG. 1 is a diagram showing a configuration of a cell analyzer according to Embodiment 1.

As shown in FIG. 1, a cell analyzer 10 includes a light source unit 11, a shutter 12, a ¼ wave plate 13, a beam expander 14, a condenser lens 15, a dichroic mirror 16, an objective lens 17, a stage 18, an image capturing unit 19, controllers 20, 21, and an information processing apparatus 100. The image capturing unit 19 includes a condenser lens 19a and an image pickup device 19b. The image pickup device 19b is a CCD, an EMCCD, a CMOS, or a scientific CMOS image sensor, for example.

A glass slide 22 having a sample placed thereon is set on the stage 18. The sample includes test cells, and first substances and second substances are included in the nucleus of each test cell. Each of the first substances and the second substances to be detected is a biogenic substance such as a gene, a protein, or a peptide which serves as a disease marker, for example. Specifically, in Embodiment 1, the test cells are collected from a lesion tissue. The first substance is HER-2 gene and the second substance is the centromere region of chromosome 17 (CEP17). HER-2 gene is a disease marker for breast cancer. In normal cells, CEP17 is present by the same number as that of HER-2 gene, and does not proliferate even when the patient has breast cancer or the like. Thus, CEP17 is used as an internal control which serves as a reference based on which amplification of HER-2 gene is measured.

In a sample, first fluorescent dyes are bound to the first substances, and second fluorescent dyes are bound to the second substances. Each first fluorescent dye is switchable between an active state in which the first fluorescent dye generates fluorescence by being irradiated with light from a light source 11a, and an inactive state in which the first fluorescent dye does not generate fluorescence even when irradiated with light from the light source 11a. The first fluorescent dye is inactivated when irradiated with light from the light source 11a, and is activated when irradiated with light from a light source 11c. In the following, "to inactivate" is referred to as "to quench". The nucleus of each test cell is stained by third fluorescent dyes.

In Embodiment 1, by means of light from the light source 11c, the first fluorescent dyes are activated from a quenched state. Light from the light source 11c is also used to excite the third fluorescent dyes to generate fluorescence. In this manner, since light from the light source 11c can be used in common for activation of the first fluorescent dyes and excitation of the third fluorescent dyes, the configuration of the cell analyzer 10 can be simplified. Activation of the first fluorescent dyes may be caused by the action of heat, chemical agent, or the like, instead of the action of light.

The light source unit 11 applies light to each test cell. The light source unit 11 includes the light sources 11a, 11b, 11c, and dichroic mirrors 11d, 11 e. The light sources 11a, 11 b, 11c emit lights having different wavelengths, respectively. As the light source unit 11, a laser light source is preferably used, but a mercury lamp, a xenon lamp, an LED, or the like may be used. The dichroic mirror 11d allows light emitted from the light source 11b to pass therethrough, and reflects light emitted from the light source 11a. The dichroic mirror 11e allows lights emitted from the light sources 11a, 11b to pass therethrough, and reflects light emitted from the light source 11c. The optical axes of lights emitted from the light sources 11a, 11 b, 11c are caused to be aligned with one another by the dichroic mirrors 11d, 11 e. Usually, the light sources in the light source unit 11 are preferably arranged such that the wavelength of light emitted from the light source 11b is longest, and the wavelength of light emitted from the light source 11c is shortest.

The light source unit 11 applies light to each test cell, to cause fluorescence to be generated from the test cell. Specifically, lights emitted from the light sources 11a, 11b, 11c respectively excite the first fluorescent dyes, the second fluorescent dyes, and the third fluorescent dyes contained in the test cell to generate fluorescence.

The shutter 12 is driven by the controller 20, and performs switching between a state in which light emitted from the light source unit 11 is allowed to pass therethrough, and a state in which light emitted from the light source unit 11 is blocked. Accordingly, the irradiation time period of light applied to the test cell is adjusted. The ¼ wave plate 13 converts linearly polarized light emitted from the light source unit 11 into circularly polarized light. A fluorescent dye reacts with light in a predetermined polarization direction. Thus, by converting light for excitation into circularly polarized light, the polarization direction of the light for excitation can be easily aligned with the polarization direction in which the fluorescent dye reacts. Accordingly, each fluorescent dye contained in the test cell can be efficiently excited to emit fluorescence. The beam expander 14 widens the light irradiation region on the glass slide 22. The condenser lens 15 collets light such that collimated light is applied to the glass slide 22 from the objective lens 17. The shutter 12 and the ¼ wave plate 13 may be arranged immediately downstream of the light sources 11a, 11b, and 11c.

The dichroic mirror 16 reflects light emitted from the light source unit 11, and allows fluorescence generated from the test cell to pass therethrough. The objective lens 17 guides to the glass slide 22 the light reflected by the dichroic mirror 16. The stage 18 is driven by the controller 21 and moves in a horizontal plane. Accordingly, light is widely applied to the glass slide 22. Fluorescence generated from the test cell passes through the objective lens 17, and passes through the dichroic mirror 16. The condenser lens 19a collets the fluorescence and guides the fluorescence to the light receiving surface of the image pickup device 19b. The image pickup device 19b captures an image of the fluorescence and outputs the captured image.

The information processing apparatus 100 is a personal computer and includes a body 110, a display unit 120, and an input unit 130. The body 110 includes a processing unit 111, a storage unit 112, and an interface 113.

The processing unit 111 is a CPU, for example. The storage unit 112 is a ROM, a RAM, a hard disk, or the like. The processing unit 111 performs various functions on the basis of programs stored in the storage unit 112. The processing unit 111 processes images obtained from the image pickup device 19b, and performs other various processes. In addition, through the interface 113, the processing unit 111 controls the light sources 11a, 11b, 11c of the light source unit 11, the image pickup device 19b, and the controllers 20, 21. The display unit 120 is a display for displaying results and the like of processes performed by the processing unit 111. The input unit 130 is composed of a keyboard and a mouse for receiving input of instructions from a user.

Hereinafter, a first processing step and a second processing step performed by the processing unit 111 are described. In the following, the captured images of fluorescences excited from the first fluorescent dyes, the second fluorescent dyes, and the third fluorescent dyes are respectively referred to as "first image", "second image", and "third image". The wavelength, the intensity, and the irradiation time period of each light described in the explanation of the first processing step and the second processing step are applied when the corresponding one of the first fluorescent dyes, the second fluorescent dyes, and the third fluorescent dyes is used in "(3) Experiment" described below. If the first fluorescent dyes, the second fluorescent dyes, and the third fluorescent dyes are changed, or if the dye labeling method or the labeling density is changed, the wavelength, the intensity, and the irradiation time period of each light are changed as appropriate, accordingly.

(1) First Processing Step

Figure 2B:
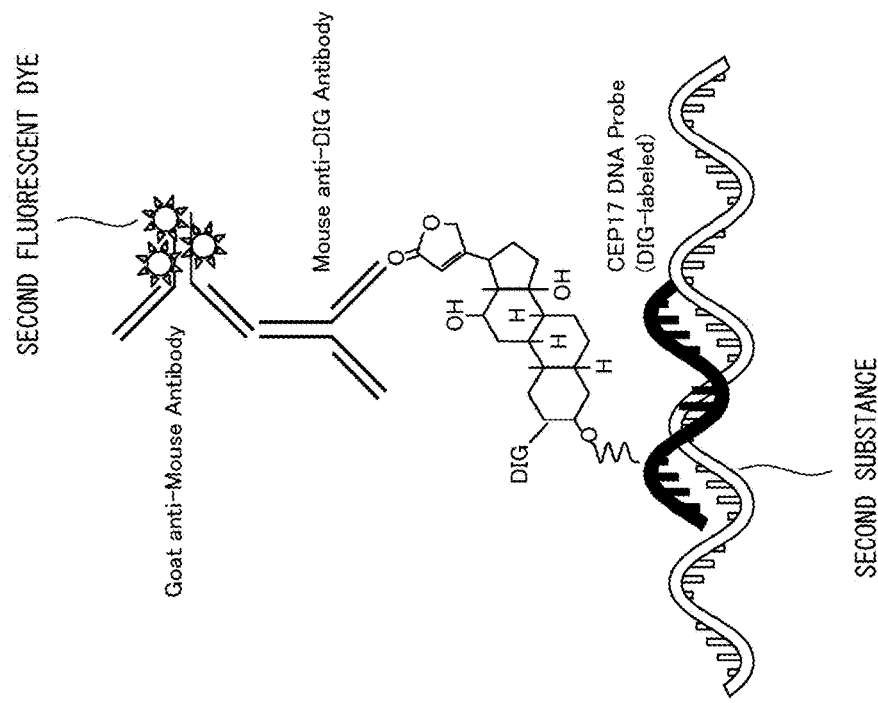
FIG. 2B is a diagram showing a state in which a second fluorescent dye is bound to a second substance according to Embodiment 1.
Figure 2A:
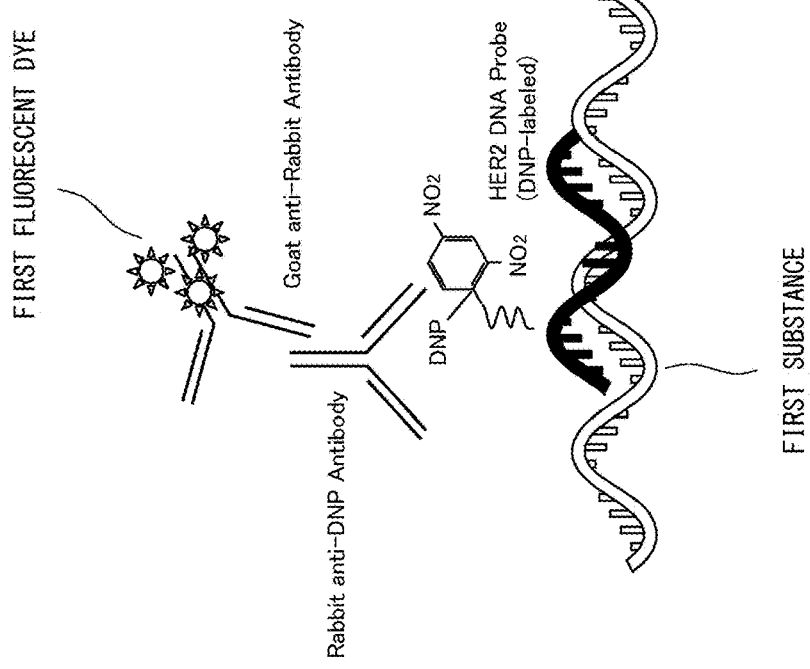
FIG. 2A is a diagram showing a state in which a first fluorescent dye is bound to a first substance according to Embodiment 1.

First, with reference to FIGS. 2A and 2B, the binding form of the fluorescent dyes is described. In the first processing step, during sample preparation, the first fluorescent dyes are bound to the first substances. As shown in FIG. 2A, the first fluorescent dye is bound to the first substance via an intermediate substance that specifically binds to the first substance. During sample preparation, the second fluorescent dyes are bound to the second substances. As shown in FIG. 2B, the second fluorescent dye is bound to the second substance, also via an intermediate substance that specifically binds to the second substance. During sample preparation, the nucleus of each test cell is specifically stained by the third fluorescent dyes. Here, in a case where the first substance or the second substance is a gene, a nucleic acid probe can be used as the intermediate substance. In a case where the first substance or the second substance is a protein, an antibody specific to the protein can be used as the intermediate substance. With respect to the substance that binds to a fluorescent dye, the target and the number thereof may be changed in accordance with the analysis purpose.

Figures 3A, 3B, 3C, 3D:
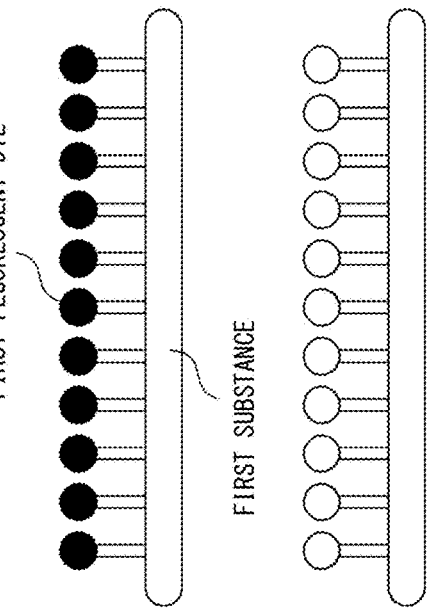
FIG. 3A is a diagram showing that all the first fluorescent dyes are in an active state according to Embodiment 1.
FIG. 3B is a diagram showing that all the first fluorescent dyes are in a quenched state according to Embodiment 1.
FIG. 3C is a diagram showing that a part of the first fluorescent dyes are in an active state according to Embodiment 1.
FIG. 3D is a diagram showing that a part of the first fluorescent dyes are in an active state according to Embodiment 1.

As schematically shown in FIG. 3A, a large number of the first fluorescent dyes are bound to one first substance. In FIG. 3A, two first substances each having the first fluorescent dyes bound thereto are schematically shown. Similarly, a large number of the second fluorescent dyes are bound to one second substance. As described above, each of the first fluorescent dye and the second fluorescent dye is a fluorescent dye switchable between the quenched state and the active state by laser light having a predetermined wavelength.

In the initial state, as schematically shown in FIG. 3A, all the first fluorescent dyes are in the active state. In FIG. 3A, the active state is indicated by a black circle. In this state, when light from the light source 11a is applied to the test cell for a predetermined time period, all the first fluorescent dyes are quenched as shown in FIG. 3B. In FIG. 3B, the quenched state is indicated by a white circle.

Then, when light from the light source 11c is applied to the test cell for a predetermined time period, a part of the first fluorescent dyes are activated as shown in FIG. 3C, for example. Through adjustment of the irradiation time period of the light from the light source 11c, the proportion of the first fluorescent dyes to be activated is changed. When light from the light source 11a is applied to the test cell for a predetermined time period, again, all the first fluorescent dyes are quenched as shown in FIG. 3B. Then, when light from the light source 11c is applied to the test cell for a predetermined time period, again, a part of the first fluorescent dyes are activated as shown in FIG. 3D, for example. As shown in FIGS. 3C and 3D, the distribution of the first fluorescent dyes activated through the activation process each time is different.

In the first processing step, the first fluorescent dyes are quenched once, then, activated again, and then, irradiated with light for excitation, and an image of fluorescence is captured. Thus, the first image is obtained in a state where the first fluorescent dyes sparsely emit fluorescence, as shown in FIG. 3C, for example. The second fluorescent dyes are switchable between the quenched state and the active state, but in the first processing step, an image of the second fluorescent dyes is captured in the initial state, without being quenched. Therefore, the second image is obtained in a state where all the second fluorescent dyes emit fluorescence as shown in FIG. 3A.

In the first processing step, the wavelengths of lights emitted from the light sources 11a, 11b, 11c are 640 nm, 730 nm, and 405 nm, respectively.

Figure 4B:
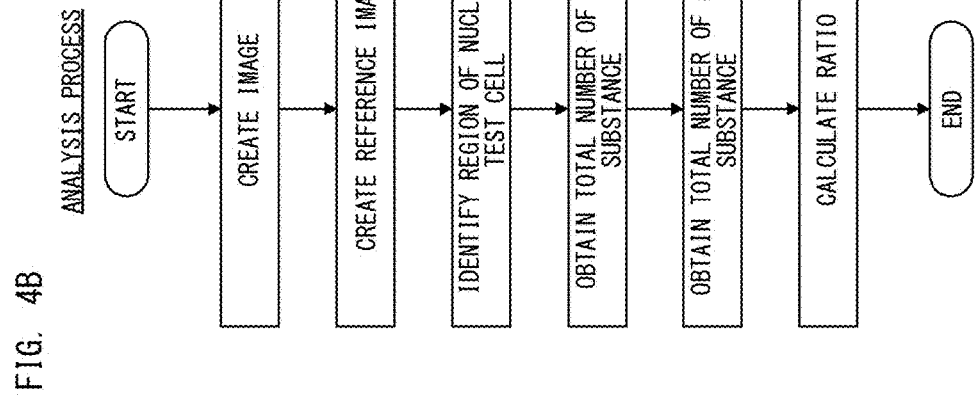
FIG. 4B is a flow chart showing an analysis process in a first processing step according to Embodiment 1.
Figure 4A:
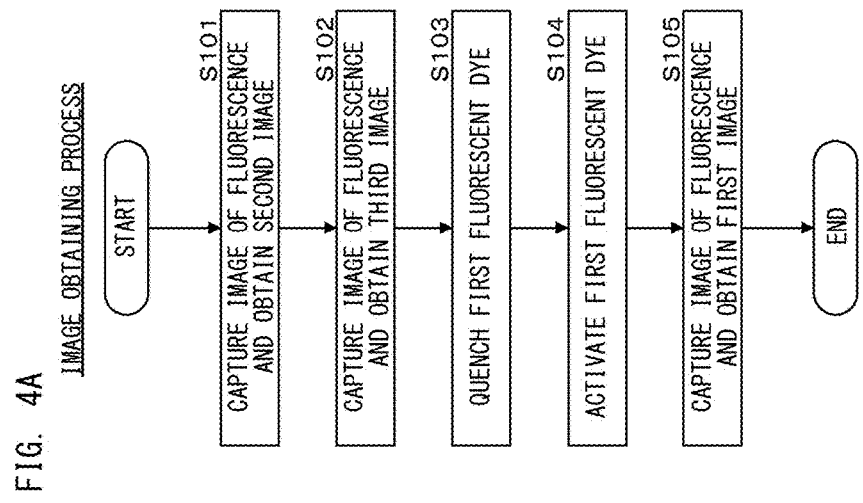
FIG. 4A is a flow chart showing an image obtaining process in a first processing step according to Embodiment 1.

As shown in FIG. 4A, in step S101, the processing unit 111 causes light from the light source 11b to be applied to the test cell at 20 mW for 1.5 seconds, thereby to cause fluorescence to be generated from the second fluorescent dyes, and causes the image capturing unit 19 to capture an image of the generated fluorescence. The processing unit 111 repeats the image capturing while the light is applied to the test cell, and obtains 100 second images. It should be noted that, in step S101, 100 second images are obtained, but the number of images to be obtained is not limited thereto, and one image may be obtained, for example.

In step S102, the processing unit 111 causes light from the light source 11c to be applied to the test cell at 1 mW for 1.5 seconds, thereby to cause fluorescence to be generated from the third fluorescent dyes, and causes the image capturing unit 19 to capture an image of the generated fluorescence. The processing unit 111 repeats the image capturing while the light is applied to the test cell, and obtains 100 third images. It should be noted that, in step S102, 100 third images are obtained, but the number of images to be obtained is not limited thereto, and one image may be obtained, for example.

In step S103, the processing unit 111 causes light from the light source 11a to be applied to the test cell at 80 mW, thereby to cause the first fluorescent dyes to be quenched. In step S104, the processing unit 111 causes light from the light source 11c to be applied to the test cell at 15 mW for 0.15 seconds, thereby to activate the first fluorescent dyes. In step S105, the processing unit 111 causes light from the light source 11a to be applied to the test cell at 80 mW for 2 seconds, thereby to cause fluorescence to be generated from the first fluorescent dyes, and causes the image capturing unit 19 to capture an image of the generated fluorescence. While the light is applied to the test cell, the processing unit 111 repeats the image capturing and obtains 100 first images. In step S105, since the light that is the same as that in step S103 is used, the first fluorescent dyes are quenched while the light is applied in step S105. Then, an image obtaining process of the first processing step ends. It should be noted that, in step S105, 100 first images are obtained, but the number of images to be obtained is not limited thereto, and one image may be obtained, for example.

Then, in step S111 shown in FIG. 4B, the processing unit 111 creates diffraction-limited images of the first fluorescent dyes, the second fluorescent dyes, and the third fluorescent dyes, on the basis of the first images, the second images, and the third images, respectively. Hereinafter, the diffraction-limited image of the fluorescent dyes obtained through quenching and reactivation is particularly referred to as "reactivation diffraction-limited image".

As shown in FIG. 5A, the reactivation diffraction-limited image is created by averaging images obtained by performing quenching and activation only once as shown in steps S103 to S105 in FIG. 4A. Thus, the reactivation diffraction-limited image of the first fluorescent dyes is created by averaging 100 first images obtained in step S105.

As shown in FIG. 5B, the diffraction-limited image is created by averaging images obtained without performing quenching and activation as shown in steps S101 and S102 in FIG. 4A. Thus, the diffraction-limited image of the second fluorescent dyes is created by averaging the plurality of the second images obtained in step S101. The diffraction-limited image of the third fluorescent dyes is created by averaging the plurality of the third images obtained in step S102.

With reference back to FIG. 4B, in step S112, the processing unit 111 creates a reference image by superposing the three images obtained in step S111. The reference image is displayed on a screen on which a determination result described below is displayed. In step S113, the processing unit 111 identifies the region of the nucleus of the test cell on the basis of the diffraction-limited image of the third fluorescent dyes obtained n step S111.

In step S114, the processing unit 111 obtains the total number of the first substances. Specifically, as shown in FIG. 5A, the processing unit 111 calculates the total area of fluorescence regions in the region of the nucleus of the test cell obtained in step S113, in the reactivation diffraction-limited image of the first fluorescent dyes obtained in step S111. Subsequently, the processing unit 111 divides the calculated total area of the fluorescence regions by the area of a fluorescence region corresponding to one first substance and stored in advance in the storage unit 112, and uses the division result as the total number of the first substances. It should be noted that how to obtain the total number of the first substances is not limited to the method of dividing the total area of the fluorescence regions by a unit area. For example, the approach shown in FIG. 7 to be used in the second processing step described below may be applied to 100 first images, to obtain the total number of the first substances.

With reference back to FIG. 4B, in step S115, the processing unit 111 obtains the total number of the second substances in a similar manner to that in step S114. That is, the processing unit 111 calculates the total area of the fluorescence regions in the region of the nucleus of the test cell obtained in step S113, in the diffraction-limited image of the second fluorescent dyes obtained in step S111. Subsequently the processing unit 111 divides the calculated total area of the fluorescence regions by the area of a fluorescence region corresponding to one second substance and stored in advance in the storage unit 112, and uses the division result as the total number of the second substances. The order of the process of step S114 and the process of step S115 may be inversed.

In step S116, the processing unit 111 calculates the ratio of the total number of the first substances to the total number of the second substances, i.e., "the number of the first substances/the number of the second substances". For example, in a case where 30 test cells are contained in the captured image, the processing unit 111 calculates the ratio by dividing the total number of the first substances in the 30 test cells by the total number of the second substances in the 30 test cells. Then, the analysis process in the first processing step ends.

In step S116, the processing unit 111 may calculate the ratio by dividing the number of the first substances in one test cell by the number of the second substances in one test cell. In this case, the processing unit 111 obtains the number of the first substances in one test cell, by averaging the numbers of the first substances obtained for the respective test cells. Further, the processing unit 111 obtains the number of the second substances in one test cell, by averaging the numbers of the second substances obtained for the respective test cells.

(2) Second Processing Step

In the first processing step, during the image capturing, with respect to the first fluorescent dyes, the quenching process and the reactivation process are each performed only once. However, in the second processing step, with respect to the first fluorescent dyes, a quenching process, a reactivation process, and an image capturing process are repeated a plurality of times, whereby the first images are obtained. In addition, in the second processing step, bright points are extracted from each obtained first image, the extracted bright points are classified into groups each corresponding to a first substance, whereby the number of the first substances is obtained.

It should be noted that the second processing step is assumed to be subsequently performed after the image obtaining process and the analysis process in the first processing step have been performed. Therefore, in the second processing step, at the start of the image obtaining process, a state has been established where the first fluorescent dyes have been quenched through the image capturing process of the first processing step, i.e., step S105 in FIG. 4A. In a case where the processes of the second processing step are independently performed, i.e., not following the first processing step, step S101 to S103 in FIG. 4A are added before step S121 in FIG. 6A, step S113 in FIG. 4B is added in the latter stage of step S132 in FIG. 6B, and step S115 in FIG. 4B is added in the latter stage of step S133 in FIG. 6B.

Figure 6B:
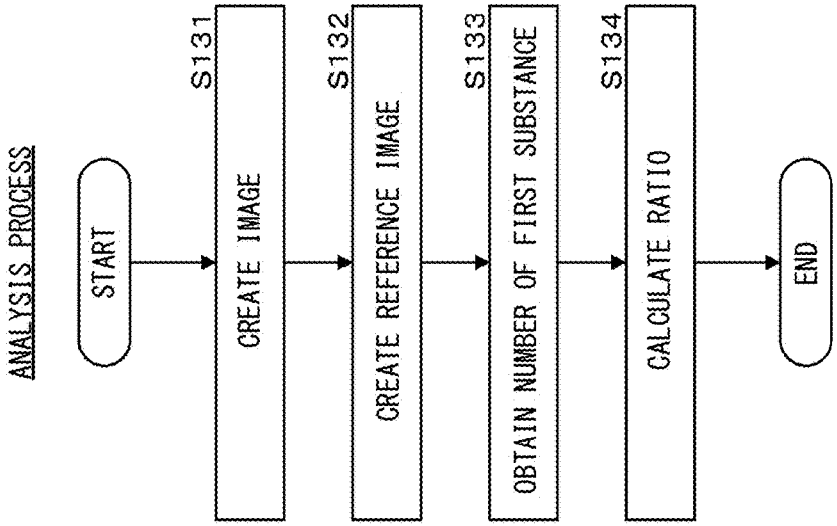
FIG. 6B is a flow chart showing an analysis process in a second processing step according to Embodiment 1.
Figure 6A:
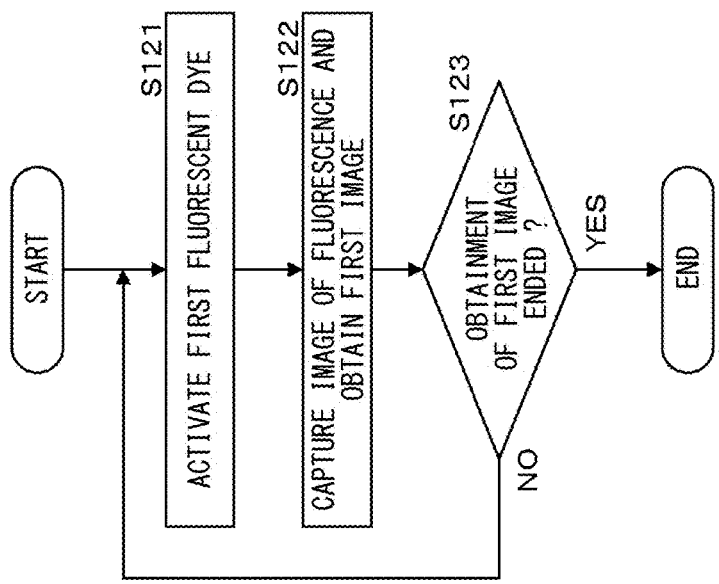
FIG. 6A is flow chart showing an image obtaining process in a second processing step according to Embodiment 1.

As shown in FIG. 6A, in step S121, the processing unit 111 causes light to be applied from the light source 11c to the test cells at 15 mW for 0.15 seconds, thereby to activate the first fluorescent dyes. In step S122, the processing unit 111 causes light to be applied from the light source 11a to the test cells at 80 mW for 2.25 seconds, thereby to cause fluorescence to be generated from the first fluorescent dyes, and causes the image capturing unit 19 to capture an image of the generated fluorescence. While the light is applied to the test cells, the processing unit 111 repeats the image capturing and obtains 100 first images. In step S122, while the light is applied, the first fluorescent dyes are quenched.

In step S123, the processing unit 111 determines whether the obtainment of the first image has ended. The processing unit 111 repeats the processes of steps S121 and S122 a predetermined number of times. Here, the processes of steps S121 and S122 are repeated 29 times. In this manner, the processing unit 111 obtains 3000 first images, which is the total of 100 first images obtained in step S105 in FIG. 4A and 2900 first images obtained by repeating the processes of steps S121 and S122, 29 times.

As shown in FIG. 6B, in step S131, the processing unit 111 creates a super-resolution image of the first fluorescent dyes.

Figure 7:
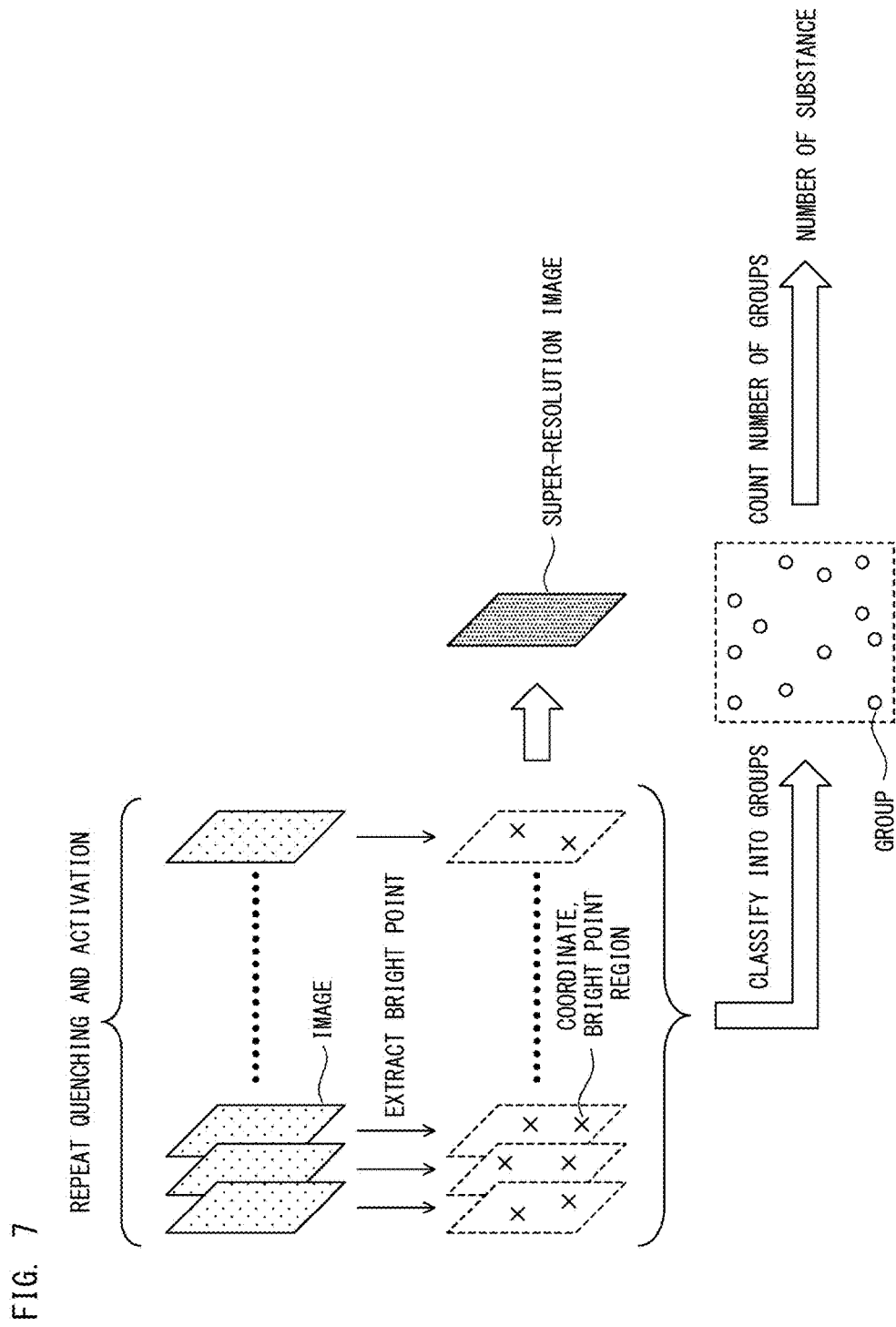
FIG. 7 is a diagram describing a procedure of obtaining a super-resolution image and the number of substances according to Embodiment 1.

As shown in FIG. 7, the super-resolution image is created on the basis of the first images obtained through steps S103 to S105 in FIG. 4A and steps S121 to S123 in FIG. 6A. Specifically, for each first image, bright points of fluorescence are extracted through Gauss fitting. Accordingly, on a two-dimensional plane, coordinates of each bright point is obtained. Here, for each fluorescence region on a first image, if matching with a reference waveform is obtained in a predetermined range through Gauss fitting, a bright point region having a width corresponding to this range is assigned to each bright point. With respect to a bright point in a fluorescence region that matches, at one point, with the reference waveform, a bright point region having a lowest-level width is assigned. Thus obtained bright point regions of the respective bright points are superposed for all the first images, whereby a super-resolution image is created.

Thus, the super-resolution image of the first fluorescent dyes is created by the bright points being extracted from the 3000 first images obtained through steps S103 to S105 in FIG. 4A and steps S121 and S122 in FIG. 6A, and then by the bright point regions of the extracted bright points being superposed.

With reference back to FIG. 6B, in step S132, the processing unit 111 creates a reference image by superposing the super-resolution image of the first fluorescent dyes obtained in step S131 and the diffraction-limited image of the second fluorescent dyes and the diffraction-limited image of the third fluorescent dyes obtained in step S111 in FIG. 4B. The reference image is displayed on the screen on which a determination result described below is displayed.

In step S133, the processing unit 111 obtains the number of the first substances. Specifically, as shown in FIG. 7, the processing unit 111 classifies the bright points extracted at the creation of the super-resolution image in step S131, into groups each corresponding to one first substance. That is, first, the processing unit 111 maps all the bright points extracted from the 3000 first images, onto a coordinate plane. Next, the processing unit 111 scans the coordinate plane with a reference region having a predetermined width, and refers to the number of bright points contained in the reference region. Further, the processing unit 111 extracts the position of a reference region in which the number of bright points contained in the reference region is greater than a threshold and greater than in the surrounding area, and classifies the group of the bright points contained in the reference region at the extracted position, into a group that corresponds to a first substance. It should be noted that the method for classifying bright points into groups each corresponding to a first substance is not limited thereto. The bright points may be classified into groups each corresponding to a first substance through another clustering approach.

Here, as described with reference to FIGS. 3A to 3D, a large number of the first fluorescent dyes are bound to one first substance. In addition, as shown in FIGS. 3C and 3D, the first fluorescent dyes bound to one first substance are sparsely activated, and the distribution of the first fluorescent dyes activated through the quenching process and the activation process is different each time. Thus, the positions of the bright points that correspond to the first substances are slightly shifted for each first image. However, by grouping the bright points as described above, bright points that are close to each other and that are based on a plurality of the first fluorescent dyes bound to one first substance are classified into one group.

In step S133 in FIG. 6B, further on the coordinate plane, the processing unit 111 identifies the region of the nucleus of each test cell obtained in step S113, and counts the number of groups contained in the region of the nucleus of the test cell. Thus, the processing unit 111 obtains the counted number of the groups, as the number of the first substances. Here, when a plurality of the test cells are contained in the first image, the number of the first substances is obtained, for example, by averaging the numbers of the first substances obtained for the respective test cells.

Thus, since the region of the nucleus of each test cell is identified in step S113 in FIG. 4B on the basis of the images captured by the image capturing unit 19, the region of the nucleus of the test cell can be superposed on the bright points of the first fluorescent dyes on the images in step S133, and thus, the bright points of the first fluorescent dyes can be smoothly extracted for each region of the nucleus of the test cell. Accordingly, the number of the first substances can be smoothly obtained.

In step S134, the processing unit 111 calculates the ratio of the number of the first substances obtained in step S133, to the number of the second substances in one test cell, i.e., "the number of the first substances/the number of the second substance". The number of the second substances in one test cell is obtained by dividing the total number of the second substances obtained in step S115 in FIG. 4B, by the number of the nuclei in the test cells. Then, the analysis process in the second processing step ends. It should be noted that the number of the first images obtained in step S122 in FIG. 6A is not limited to 100, and may be another number.

In the description below, in a case where the number of the first substances and the number of the second substances for each nucleus are to be obtained on the basis of the total number of the first substances and the total number of the second substances obtained in steps S114 and S115 of the first processing step, a process of dividing the total number of the first substances and the total number of the second substances by the number of the nuclei in the test cells is performed, similarly to step S134.

As described above, when the activation process is performed after the inactivation process of quenching the first fluorescent dyes has been performed, only a part of the first fluorescent dyes bound to each first substance are activated. In addition, it could happen that the first fluorescent dyes not having been activated by the activation process last time are activated by the activation process this time. Therefore, by repetition of the inactivation process, the activation process, and the image capturing process a plurality of times, the first fluorescent dyes can be caused to emit light evenly, and at the same time, fluorescence of the first fluorescent dyes can be caused to be dispersed in each first image. Thus, from each first image, bright points based on the first fluorescent dyes can be smoothly extracted. Then, by the classification of the extracted bright points into groups each corresponding to a first substance, the number of the first substances can be counted. Accordingly, the number of the first substances in the test cells can be accurately counted.

It should be noted that, in the first processing step and the second processing step, it is necessary to adjust the intensity of light for activation emitted from the light source 11c so that the first fluorescent dyes can be detected at one-molecule level. In the case of Embodiment 1, activation efficiency was increased in proportion to the product of the intensity of the activation light and the exposure time period of the activation light, and the activation efficiency was saturated at a certain level. The activation efficiency means the proportion of the first fluorescent dyes activated through one activation process, in the quenched first fluorescent dyes. The activation efficiency for accurately detecting the first fluorescent dyes is not higher than 20%, and preferably not higher than 10%. If the intensity of the activation light and the exposure time period of the activation light are adjusted so as to realize a desired value of the activation efficiency, the first fluorescent dyes can be accurately detected.

In a case where the activation efficiency is set to be low as above, in order to activate all the first fluorescent dyes and perform detection thereof, the greater the number of times of repeating the quenching and activation, the better. However, a greater number of times of repeating results in a long measurement time period. Thus, in Embodiment 1, in order to make the measurement time period as short as possible, the total number of times of repeating the quenching and the activation through the first processing step and the second processing step is set to 30. The number of times of repeating the quenching and the activation is not limited to 30, and can be set to a desired number of times in consideration of the activation efficiency and the measurement time period. When there is no need to detect the first fluorescent dyes at one-molecule level, the activation efficiency may be higher than or equal to 50%. The activation efficiency is determined depending on the density in the test cells.

(3) Experiment

Next, an experiment performed by the inventors is described. In the experiment, for convenience, a type of dye that is switchable between the quenched state and the active state was used as the second fluorescent dyes. However, since the second fluorescent dyes are not quenched in the first and second processing steps in Embodiment 1 as described above, a non-switchable type of fluorescent dye may be used. As such a type of second fluorescent dye, a fluorescent dye such as Cy2 can be used, for example.

<Creation of FISH Stained HER-2 Sample>

Experiment samples were created through the following steps.

By use of Ventana Inform Dual ISH HER-2 kit (manufactured by Roche Diagnostics K.K.), staining was performed on HER-2 gene amplification positive calu-3 and HER-2 gene amplification negative MCF7 cells on HER-2 Dual ISH 3-in-1 Control Slide (Ventana).

[FFPE Sample Preparation Step]

The control slide was dried on Dry Block Bath THB (AS ONE) at 65° C. for 20 minutes. Ez Prep was placed on the slide and deparaffinization was performed at 75° C. for 5 minutes. This operation was repeated 5 times, and then the slide was immersed in Reaction Buffer. Dry Block Bath THB was set at 90° C., CC2 was dropped thereto, and then, conditioning was performed for 10 minutes. CC2 was added as appropriate so as to prevent the slide from drying. This operation was performed 3 times, and then, the slide was immersed in Reaction Buffer for 4 minutes. This operation was repeated 3 times. On the slide, ISH Protease II was dropped by 80 μL, a cover glass was placed thereon, and the slide was subjected to an enzymatic treatment for 16 minutes in a moist chamber placed in an incubator at 37° C.

The slide was immersed in 2×SSC for 4 minutes 3 times to be washed. HybReady and HER-2 DNA cocktail probes were mixed, and the mixture was dropped by 30 μL on the slide, covered with a cover glass, and then sealed with paper bond. The slide was placed on Dry Block Bath THB, and thermal denaturation was performed thereon at 95° C. for 20 minutes. Then, hybridization was performed on the slide overnight on DryBlock Bath THB at 44° C. The slide was immersed in 2×SSC at 62° C. for 4 minutes to be washed. This operation was repeated 3 times, and the slide was immersed in Reaction Buffer. 1% BSA/Reaction buffer was dropped on the slide by 500 μL, and blocking was performed on the slide for 20 minutes in a moist chamber placed in an incubator at 37° C. The slide was immersed in Reaction buffer to be washed.

[Staining Step]

Rabbit Anti DNP Antibody and Mouse Anti DIG Antibody were mixed together, and the mixture was dropped on the slide, covered with a cover glass, and allowed to react for 20 minutes in a moist chamber placed in an incubator at 37° C. The slide was immersed in Reaction Buffer for 3 minutes to be washed. This operation was performed 3 times. Alex-aFluor 647 F(ab')$_2$ fragment of goat anti-rabbit IgG (H+L) (Life Technologies, A-21246), AlexaFluor 750 GoatAnti Mouse IgG(H+L) (Life Technologies, A-21037), and Hoechst 33342 (Life Technologies, H1399) (100 mg was diluted in PBS 10 mL and preserved) were diluted by 1000-fold with 1% BSA/Reaction buffer. The resultant mixture was dropped to the slide by 80 μL, covered with a cover glass, and allowed to react for 20 minutes in a moist chamber placed in an incubator at 37° C. The slide was immersed in TBST for 3 minutes to be washed. This operation was performed 3 times. The slide was immersed in PBS for 3 minutes to be washed. This operation was performed 3 times. The slide was immersed in purified water to be washed. This operation was performed twice, and the slide was dried for 15 minutes in an incubator at 37° C.

Alexa Fluor 647 corresponds to the first fluorescent dyes described above. Alexa Fluor 750 corresponds to the second fluorescent dyes described above. Hoechst 33342 corresponds to the third fluorescent dyes described above.

[Image Capture Preparatory Step]

0.04 μm FluoSphere Dark Red (life technology, F8789) was diluted with PBS, and the mixture was dropped to the slide by 50 μL, covered with a cover glass, and left still for 10 minutes. The slide was washed with 500 μL of PBS, a mount medium was dropped by 50 μL, a cover glass was placed thereon and fixed with manicure. The composition of the mount medium was as follows.

1M Tris (pH 7.4) 5 μL, 1M NaCl 1 μL, 25% glucose 40 μL, 2-mercaptoethanol 1 μL, 5000 U/mL Glucose Oxidase 1 μL, 1000 μg/mL catalase 1 μL, H2O 51 μL <Process Result of First Processing Step>

The processes according to the first processing step were performed on the sample above. Reference images created in step S112 in FIG. 4B of a sample based on HER-2 gene amplification positive calu-3 are shown in FIGS. 8A to 8D. In FIGS. 8A to 8D, each dotted arrow indicates the first substance, i.e., HER-2 gene, and each thick arrow indicates the second substance, i.e., CEP17.

Through the process of the first processing step, the ratio calculated in step S116 in FIG. 4B was 6.12 in the case of a sample based on HER-2 gene amplification positive calu-3, and was 0.83 in the case of a sample based on HER-2 gene amplification negative MCF7 cells. According to a breast cancer guideline, the ratio greater than 2.2 means positive, the ratio smaller than 1.8 means negative, and the ratio not smaller than 1.8 and not greater than 2.2 means borderline. Therefore, through the processes of the first processing step, a positive sample can be appropriately determined as positive, and a negative sample can be appropriately determined as negative.

<Process Result of Second Processing Step>

Next, the processes according to the second processing step were further performed on the sample above. Reference images created in step S132 in FIG. 6B of a sample based on HER-2 gene amplification positive calu-3 are shown in FIGS. 9A to 9D. Reference images created in step S132 in FIG. 6B in the case of a sample based on HER-2 gene amplification negative MCF7 cells are shown in FIGS. 9E to 9G. Also in FIGS. 9A to 9G, similarly to FIGS. 8A to 8D, each dotted arrow indicates the first substance, i.e., HER-2 gene, and each thick arrow indicates the second substance, i.e., CEP17.

Through the processes of the second processing step, the ratio calculated in step S134 in FIG. 6B was 6.42 in the case of a sample based on HER-2 gene amplification positive calu-3, and was 1.18 in the case of a sample based on HER-2 gene amplification negative MCF7 cells. Therefore, also through the second processing step, a positive sample can be appropriately determined as positive, and a negative sample can be appropriately determined as negative.

<Comparative Example>

Next, as Comparative Example 1, a process was performed in which, with respect to a sample based on HER-2 gene amplification positive calu-3, a reference image was obtained without performing the quenching and the activation thereon. Reference images created in Comparative Example 1 are shown in FIGS. 10A to 10D.

At this time, the calculated ratio was 7.48 in the case of a sample based on HER-2 gene amplification positive calu-3, and was 1.16 in the case of a sample based on HER-2 gene amplification negative MCF7 cells. Therefore, also in Comparative Example 1, a positive sample can be appropriately determined as positive, and a negative sample can be appropriately determined as negative.

Next, as Comparative Example 2, a process was performed in which, with respect to a sample based on HER-2 gene amplification positive calu-3, a reference image was obtained by use of a confocal laser scanning microscope, without performing the quenching and the activation thereon. Reference images created in Comparative Example 2 are shown in FIGS. 10E to 10G. In Comparative Example 2, images of the second substances, i.e., of CEP17 were not obtained.

When the reference images according to the first processing step shown in FIGS. 8A to 8D are compared with the reference images according to Comparative Examples 1, 2 shown in FIGS. 10A to 10G, it is seen that the bright points corresponding to HER-2 gene are more separated in the first processing step. When the reference images according to the first processing step shown in FIGS. 8A to 8D are compared with the reference image according to the second processing step shown in FIGS. 9A to 9D, it is seen that the bright points corresponding to HER-2 gene are further separated in the second processing step.

According to the reference images of FIG. 8A to FIG. 9D, even in the case of a sample based on HER-2 gene amplification positive calu-3, CEP17 as the second substance is less in number, and is well separated spatially. Thus, with respect to the second fluorescent dyes which each bind to CEP17, the fluorescence regions were identified at high resolution, without through a step of reactivation after quenching thereof. Thus, with respect to the second substances for which fluorescence regions can be identified without through the step of quenching and reactivation, by obtaining the second image without performing an inactivation process of quenching the second fluorescent dyes, the process can be simplified.

<Other Examination>

In the experiment according to the processes of the second processing step, as shown in the regions surrounded by the squares in FIGS. 9B and 9D, portions in which bright point regions based on the first fluorescent dyes were connected in a line shape were observed. According to examination by the inventors, also when the other HER-2 gene amplification positive test cells were examined through the processes of the second processing step, similarly to FIGS. 9B and 9D, portions in which bright point regions were connected in a line shape were observed in a super-resolution image. The reason of this is considered as follows: in association with progress of breast cancer, amplification of HER-2 gene as the first substance became significant, the distance between HER-2 genes is reduced, and thus, the bright point regions are shown as being connected in a line shape. Thus, with respect to breast cancer, disease condition judgement and therapeutic strategy decision can be accurately performed by further performing determination on the basis of information regarding the location of the first substances, i.e., the distance between the first substances, together with the determination based on the ratio described above. This determination is considered to be similarly applicable to other diseases than breast cancer.

Here, the distance between the first substances is focused. However, depending on the kind of the first substance, it is assumed that, in association with progress of the disease condition or the amplification, the distribution state such as the position, the size, or the like of the first substances could be changed, in addition to the distance between the first substances. Therefore, disease condition judgement and therapeutic strategy decision are considered to be accurately performed by further performing determination on the basis of the distribution state of the first substances.

(4) Display Process in Embodiment 1

In the processes of the first processing step, the total area of fluorescence regions is divided by the area of a fluorescence region that corresponds to one first substance with fluorescence, whereby the number of the first substances is obtained. In this method, when the number of the first substances is small and the distance between the first substances is large, the fluorescence regions of the respective the first substances are separated from one another in the reactivation diffraction-limited image, and thus, the number of the first substances can be relatively accurately obtained. Thus, also according to the processes of the first processing step, breast cancer negative determination can be appropriately performed.

However, when breast cancer progresses, and the number of the first substances increases, the fluorescence regions of the respective the first substances could overlap one another in the reactivation diffraction-limited image. Thus, in the processes of the first processing step, the accuracy of the determination result regarding breast cancer based on the ratio could be reduced. In contrast to this, in the processes of the second processing step, even when the number of the first substances has increased as mentioned above, the number of the first substances can be obtained with high accuracy, and thus, appropriate determination regarding breast cancer can be performed. Thus, in the display process below, first, the processes of the first processing step is performed to determine whether or not amplification of the disease marker is negative, and then, only when the determination result is not negative, the processes of the second processing step are performed.

As shown in FIG. 11, in step S141, the processing unit 111 performs the processes of the first processing step shown in FIGS. 4A and 4B. Accordingly, the processing unit 111 obtains the ratio indicating the presence/absence of amplification of the first substances, in step S116 in FIG. 4B. In step S142, the processing unit 111 performs determination regarding amplification of the disease marker on the basis of the ratio calculated in step S116 in FIG. 4B. Specifically, the processing unit 111 determines as positive when the ratio is greater than 2.2, the processing unit 111 determines as negative when the ratio is smaller than 1.8, and the processing unit 111 determines as borderline when the ratio is not smaller than 1.8 and not greater than 2.2.

Subsequently, in step S143, the processing unit 111 determines whether the determination result in step S142 is negative or not. When the determination result in step S142 is negative, then, in step S144, the processing unit 111 causes the display unit 120 to display, as therapy index information, the ratio indicating the presence/absence of amplification of the first substances obtained in the first processing step and the determination result obtained in step S142. Then, the display process ends. In this case, determination and display on the basis of the second processing step are not performed. On the other hand, when the determination result in step S142 is positive or borderline, the processing unit 111 advances the process to step S145.

In step S145, the processing unit 111 performs the processes of the second processing step shown in FIGS. 6A and 6B. In step S146, on the basis of the ratio calculated in step S134 in FIG. 6B, the processing unit 111 performs determination regarding amplification of the disease marker. The determination method is the same as in step S142. As described above, according to the second processing step, the number of the first substances is accurately counted. Thus, in step S146, on the basis of the number of the first substances accurately counted, determination regarding amplification of the first substances serving as the target molecules of the molecular target drug is performed. Accordingly, a more accurate determination result regarding disease condition can be obtained.

Subsequently, in step S147, the processing unit 111 determines whether the determination result in step S146 is positive or not. When the determination result in step S146 is positive, the processing unit 111 causes, in step S148, the display unit 120 to display therapy index information including the determination result obtained in step S146. Then, the display process ends. On the other hand, when the determination result in step S146 is negative or borderline, the processing unit 111 advances the process to step S149.

In step S149, the processing unit 111 determines whether there is a line-shaped structure of the first substances in the reference image created in step S132 in FIG. 6B. The line-shaped structure of the first substances is a structure as shown in the regions surrounded by squares in FIGS. 9B and 9D. When HER-2 genes, as the first substances, that have a distance therebetween smaller than a threshold are consecutively present by a predetermined number, the processing unit 111 determines that there is a line-shaped structure of the first substances in the reference image.

When the processing unit 111 has determined that there is a line-shaped structure of the first substances, the processing unit 111 changes, in step S150, the determination result obtained in step S146 to positive. On the other hand, when the processing unit 111 has determined that there is no line-shaped structure of the first substances, the processing unit 111 advances the process to step S148 without changing the determination result obtained in step S146. Then, the display process ends.

In each of steps S142 and S146, determination regarding breast cancer is performed on the basis of the ratio of the number of the first substances and the number of the second substances. However, determination regarding breast cancer may be performed by comparing the number of the first substances for each nucleus with a threshold. However, in a case where the balance between the number of the first substances and the number of the second substances changes in accordance with progress of the disease condition as described above, if disease condition judgement is performed also with reference to the number of the second substances together with the number of the first substances, the accuracy of disease condition judgement can be increased.

As described above, with respect to breast cancer, in association with abnormal cell division, the number of HER-2 genes as the first substances increases in the nucleus of a test cell. Accordingly, the balance between the number of HER-2 genes and the number of CEP17s changes. Thus, as in the processes described above, by performing determination regarding amplification of the disease marker on the basis of the ratio between the number of the first substances and the number of the second substances, it is possible to more accurately determine the presence/absence of amplification of the disease marker. The value indicating the balance between the number of the first substances and the number of the second substances is not limited to the ratio, and may be the difference between the number of the first substances and the number of the second substances, for example.

In the flow chart shown in FIG. 11, when the determination result according to the second processing step is not positive, the process is advanced to step S149. However, the process may be advanced to step S149 irrespective of the determination result. In addition, although the determination result as negative or borderline is changed to positive when there is a line-shaped structure, an indication that there is a line-shaped structure may be added to the determination result, without the determination result being changed.

Figure 12A:
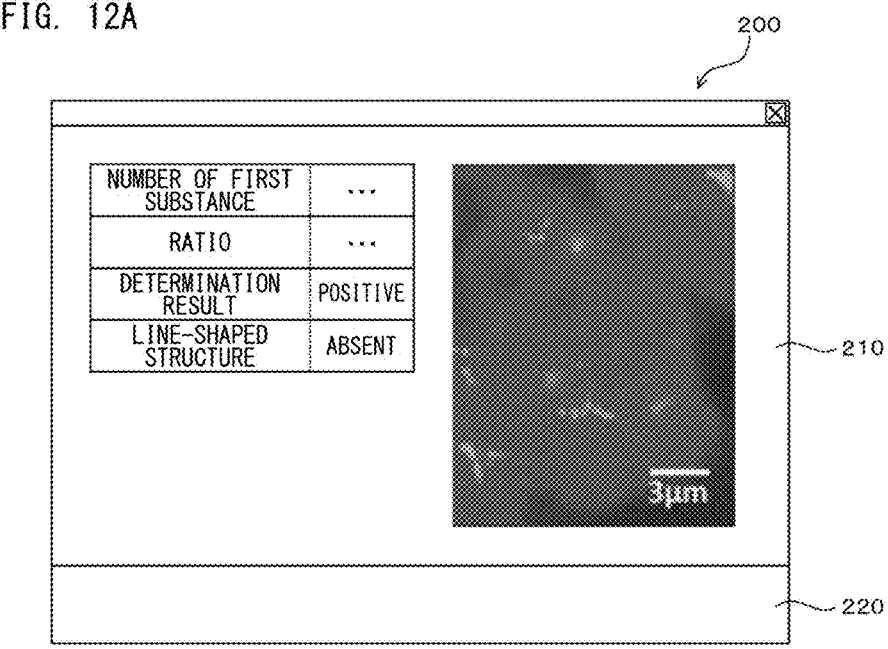
FIG. 12A is a diagram showing a configuration of a screen displayed on a display unit according to Embodiment 1.
Figure 12B:
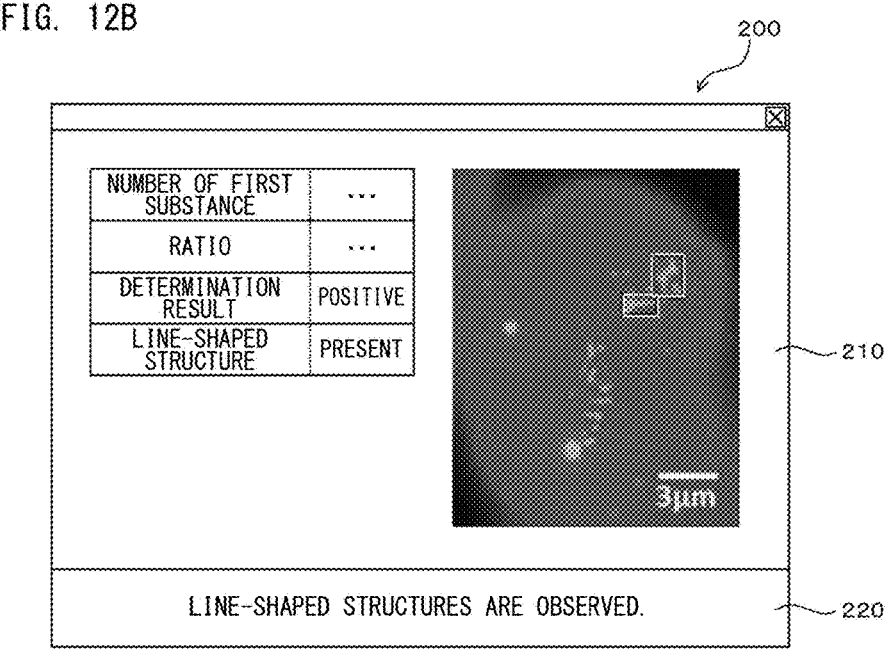
FIG. 12B is a diagram showing a configuration of a screen displayed on a display unit according to Embodiment 1.

As shown in FIGS. 12A and 12B, a screen 200 displayed on the display unit 120 in the display process includes a result region 210 and a comment region 220. In the result region 210, information obtained through the processes of the first processing step or the second processing step is displayed. Specifically, in the result region 210, therapy index information including the number of the first substances per test cell, the ratio, and the determination result regarding the disease condition relevant to the first substances; other therapy index information indicating the presence/absence of a line-shaped structure; and a reference image are displayed. In the comment region 220, supplementary description regarding the content of the result region 210 is displayed.

The screen 200 shown in each of FIGS. 12A and 12B is the one obtained when the processes of the second processing step have been performed. In FIG. 12A, no line-shaped structure is present in the test cell, and in FIG. 12B, line-shaped structures are present in the test cell.

On the screen 200 shown in FIG. 12B, a message indicating that there is a line-shaped structure in the comment region 220 is displayed. As shown in FIGS. 12A and 12B, since therapy index information including a determination result is displayed on the screen 200, the doctor or the like can perform highly accurate disease condition diagnosis without being required to perform complicated work such as counting bright points through visual observation. Since the doctor or the like is not required to be well skilled in making disease condition diagnosis, variation in diagnosis made by the doctor can be suppressed. Since the ratio between the number of the first substances and the number of the second substances is displayed in the result region 210, the doctor or the like can make a therapeutic strategy decision by referring to this ratio. It should be noted that the therapy index information to be displayed is not limited to those shown in FIGS. 12A and 12B, and the indication of the number of the first substances may be omitted, or the indication of the determination result may be omitted, for example.

When the determination result in the first processing step is not negative, a reference image obtained in the second processing step is displayed in the result region 210. This reference image has been created on the basis of the super-resolution image of the first fluorescent dyes, and thus, is a highly accurate image indicating the distribution state of bright points of the first fluorescent dyes. Thus, the doctor or the like can confirm the disease condition in more detail by referring to the distribution state of the bright points in this image.

In a case where the determination result in the first processing step is negative and the process of the second processing step is skipped, the numerical values, the determination result, and the reference image based on the processes of the first processing step are displayed in the result region 210, and the column of the line-shaped structure is masked.

As described above, in test cells of a patient who does not have breast cancer, the number of HER-2 genes is small and HER-2 genes are less likely to be close to one another. Thus, also through the image analysis in the first processing step, the number of HER-2 genes in the test cells can be accurately counted, and the fact that amplification of the first substances is negative can be accurately determined. Thus, in a case where the determination in the first processing step is negative, even if the processes of the second processing step are skipped, no problem is caused in the determination result. In addition, in this case, by the processes of the second processing step being skipped, the determination result can be provided quickly to the doctor or the like. In a case where the determination in the first processing step is not negative, the processes of the second processing step which allow more accurate counting of the number of HER-2 genes are performed, and the determination is made. Thus, a highly accurate determination result can be presented to the doctor or the like.

2. Embodiment 2

In Embodiment 2, the second fluorescent dyes are also quenched and activated similarly to the first fluorescent dyes.

Figure 13:
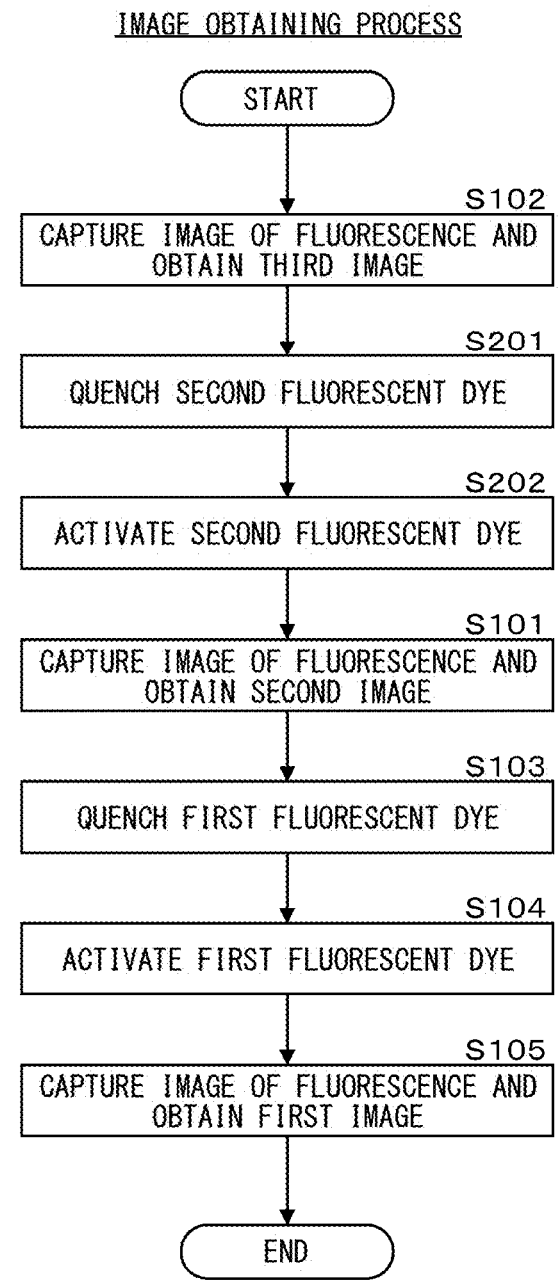
FIG. 13 is a flow chart showing an image obtaining process in a first processing step according to Embodiment 2.

As shown in FIG. 13, in Embodiment 2, steps S201 and 202 are added immediately before step S101 in the process of the first processing step in FIG. 4A. Accordingly, the second fluorescent dyes which bind to the second substances are also quenched in step S201 and then activated in step S202, and then, an image of fluorescence is captured in step S101. Through the process of step S101, the second fluorescent dyes are quenched. In this case, in step S111 in FIG. 4B, also with respect to the second substances, a reactivation diffraction-limited image is obtained similarly to the first substances, and then, in step S112, the obtained reactivation diffraction-limited image is superimposed with other images. Accordingly, in the reference image, fluorescence regions of the second substances are more separated than in Embodiment 1. As a result, the accuracy of the number of the second substances obtained in step S115 in FIG. 4B is increased. The order of the processes of steps S201, S202, and S101 and the processes of steps S103 to S105 may be inversed.

Figure 14B:
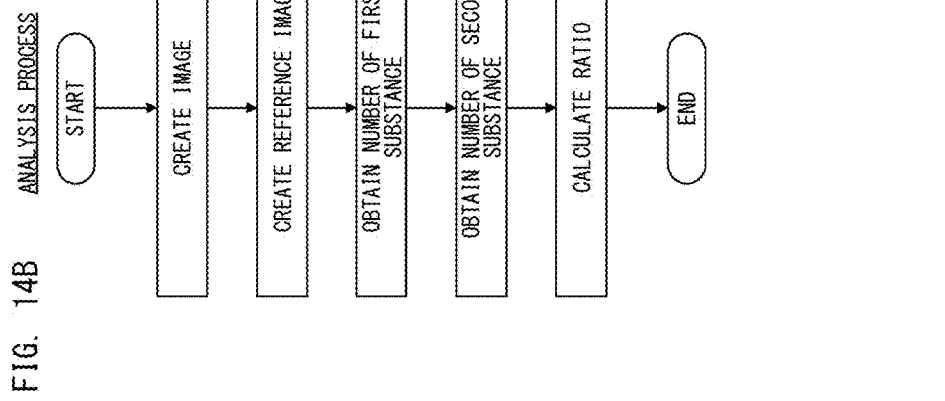
FIG. 14B is a flow chart showing an analysis process in a second processing step according to Embodiment 2.
Figure 14A:
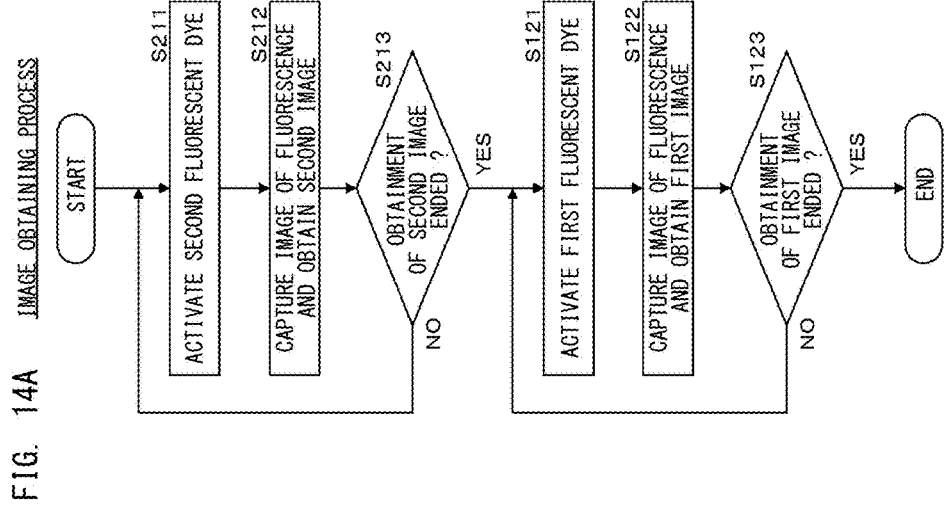
FIG. 14A is a flow chart showing an image obtaining process in a second processing step according to Embodiment 2.

As shown in FIG. 14A, in Embodiment 2, step S211 to S213 are added before step S121 in the process of the second processing step in FIG. 6A. Also with respect to the second fluorescent dyes which bind to the second substances, the process of activation in step S211 followed by image capturing and quenching in step S212 is repeated by the number of times specified in step S213, whereby a plurality of second images are obtained.

In this case, as shown in FIG. 14B, step S221 is added in the latter stage of step S133 in FIG. 6B. In step S131, also with respect to the second substances, similarly to the first substances, bright points are extracted with respect to the second images, a super-resolution image is obtained, and then, in step S132, the obtained super-resolution image is superimposed with other images. Accordingly, in the reference image, the resolution of the bright point regions of the second substances is significantly increased. In addition, in step S221, similarly to the obtainment of the number of the first substances in step S133, also with respect to the second substances, bright points are classified into groups, and the number of the second substances is obtained. Accordingly, the accuracy of the number of the second substances is increased. As a result, the accuracy of the ratio calculated in step S134 is also increased.

In Embodiment 2, quenching and activation are also performed with respect to the second fluorescent dyes. Thus, the distribution of the second substances can be displayed with higher resolution than in Embodiment 1.

In a case where amplification of the second substances in the test cells becomes significant in association with progress of the disease condition, two second substances could be close to each other. In such a case, if all the second fluorescent dyes bound to the two close second substances emit fluorescence at the same time, it becomes difficult to capture an image with fluorescences separated from one another. In Embodiment 2, also with respect to the second fluorescent dyes bound to the second substances, the step of quenching and reactivation is performed, thereby to capture an image of fluorescence. Thus, even in a case where amplification of the second substances becomes significant in association with progress of the disease condition, it is possible to capture an image in which fluorescences based on the second fluorescent dyes are separated from one another. Accordingly, the accuracy of disease condition judgement can be increased.

In a case where the super-resolution image is obtained with respect to the second substances as in Embodiment 2, the location of the second substances and the distribution state of the second substances may be obtained, similarly to the first substances. The location of the second substances corresponds to the distance between the second substances, for example. Depending on the kind of the second substance, it is assumed that, in association with the progress of the disease condition or the amplification, the distance between the second substances and the distribution state such as the position, the size, or the like of the second substances could be changed. Therefore, it is considered that, further on the basis of the distance between the second substances and the distribution state of the second substances, disease condition diagnosis and therapeutic strategy decision can be accurately performed.

<Modification>

As described above, in a case where the second fluorescent dyes are also quenched and activated, it is possible to use, as the types of the first fluorescent dye and the second fluorescent dye, switchable fluorescent dyes for which lights having different wavelengths are used for excitation, but for which a light having the same wavelength is used for activation. In this Modification, as the types of the first fluorescent dye and the second fluorescent dye, such fluorescent dyes are used.

In this case, as shown in FIG. 15A, with respect to the processes of the first processing step, steps after step S201 in FIG. 13 are changed. Lights having different wavelengths are applied to the test cells in steps S301 and S302, respectively, whereby the second fluorescent dyes and the first fluorescent dyes are quenched. Then, in step S303, light having a predetermined wavelength is applied, whereby the second fluorescent dyes and the first fluorescent dyes are activated at the same time. Then, in steps S304 and S305, lights which excite the first fluorescent dyes and the second fluorescent dyes are applied to the test cells respectively, whereby the first image and the second image are obtained. Through the processes of steps S304 and S305, the first fluorescent dyes and the second fluorescent dyes are quenched, respectively.

The process of the second processing step shown in FIG. 14A is changed as shown in FIG. 15B. In step S311, light having a predetermined wavelength is applied, whereby the second fluorescent dyes and the first fluorescent dyes are activated at the same time. Then, lights which excite the second fluorescent dyes and the first fluorescent dyes are applied to the test cells in step S312 and S313, respectively, whereby the second image and the first image are obtained. Through the processes of steps S312 and S313, the second fluorescent dyes and the first fluorescent dyes are quenched, respectively. The process of activation, image capturing, and quenching in step S311 to S313 is repeated by the number of times specified in step S314, whereby a plurality of first images and a plurality of second images are obtained.

As described above, since the activation of the quenched first fluorescent dyes and second fluorescent dyes is performed in a single step, the process is simplified. In particular, in a case where quenching and reactivation are repeated by a large number in order to obtain a super-resolution image, if the activation of the first fluorescent dyes and the second fluorescent dyes is performed in a single step, the process can be significantly simplified.

3. Embodiment 3

In Embodiment 3, a part of the optical system is changed, compared with that in Embodiment 1, and the position of each bright point in the optical axis direction of the image capturing unit 19 is obtained by the processing unit 111.

Figure 16B:
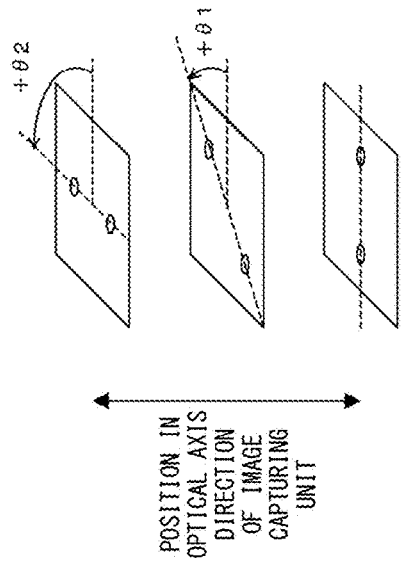
FIG. 16B is a diagram showing rotation of two focal points on a light receiving surface in accordance with the position of the light emission point of fluorescence in the optical axis direction according to Embodiment 3.
Figure 16A:
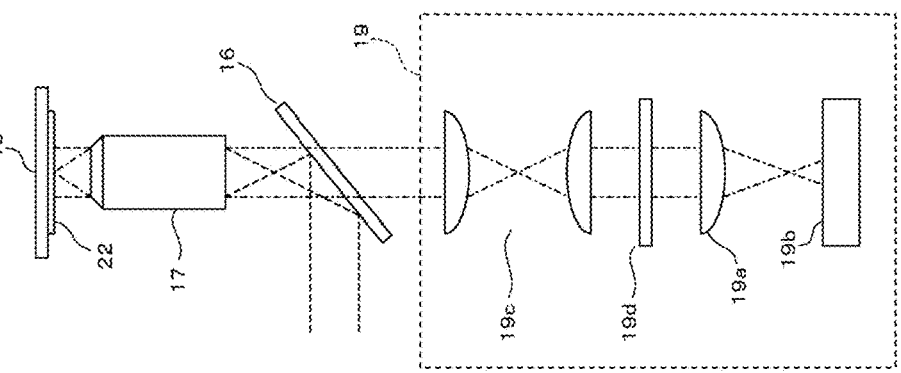
FIG. 16A is a diagram showing a configuration of a cell analyzer according to Embodiment 3.

As shown in FIG. 16A, in the cell analyzer 10, a beam expander 19c and a phase plate 19d are added to the image capturing unit 19. Fluorescence generated from a sample passes through the beam expander 19c, the phase plate 19d, and the condenser lens 19a, in order, and then an image of the fluorescence is captured by the image pickup device 19b.

The phase plate 19d is disposed at the Fourier plane, and has an action of modulating a point spread function such that two focal points appear on the light receiving surface of the image pickup device 19b. Fluorescence generated from one fluorescent dye forms an image at two focal points on the light receiving surface of the image pickup device 19b as a result of the action of the phase plate 19d. At this time, as shown in FIG. 16B, the two focal points rotate on the light receiving surface in accordance with the position of the light emission point of fluorescence in the optical axis direction of the image capturing unit 19. That is, the angle between the straight line connecting the two focal points and a straight line serving as a reference varies on the light receiving surface of the image pickup device 19b, in accordance with the position of the light emission point of fluorescence in the optical axis direction.

For example, fluorescences generated from fluorescent dyes at two different positions in the optical axis direction of the image capturing unit 19 on the glass slide 22 are each split into two by the phase plate 19d, and applied to the light receiving surface of the image pickup device 19b. At this time, as shown in FIG. 16B, for example, with respect to one fluorescent dye, the straight line connecting the two focal points on the light receiving surface forms an angle of +θ1 relative to the reference line, and with respect to the other fluorescent dye, the straight line connecting the two focal points on the light receiving surface forms an angle of +θ2 relative to the reference line. Therefore, if the angle between the straight line connecting two focal points and the reference line is obtained, the position of the fluorescent dye in the optical axis direction can be obtained.

Specifically, similarly to the second processing step, the processing unit 111 performs Gauss fitting on the first images obtained by repeating quenching and activation, to extract bright points, and further, obtains the brightness of each extracted bright point. Next, the processing unit 111 pairs two bright points that have similar brightness and the distance between which is in a predetermined range. Subsequently, the processing unit 111 performs fitting with respect to the paired two bright points against a two-bright-point template stored in advance in the storage unit 112. Then, the processing unit 111 determines two bright points that are fitted with a certain accuracy or higher, as bright points resulting from the splitting of fluorescence generated from one fluorescent dye by the phase plate 19d.

Subsequently, the processing unit 111 sets the midpoint of the paired two bright points on the light receiving surface, as the position on the two-dimensional plane at the image capture angle of the fluorescent dye. On the basis of the angle between the reference line and the straight line connecting the two bright points paired as described above, the processing unit 111 determines the position of the fluorescent dye in the optical axis direction of the image capturing unit 19. In this manner, on the basis of the positions on the two-dimensional plane and the positions in the optical axis direction, the processing unit 111 specifies coordinate points of a plurality of fluorescent dyes in the three-dimensional coordinate axes, superposes the specified coordinate points for all the first images, and thereby creates a three-dimensional super-resolution image.

Further, the processing unit 111 classifies the specified coordinate points into groups each corresponding to a first substance, thereby to obtain the number of the first substances in the test cells. In grouping of the coordinate points, for example, a predetermined reference space is caused to scan a three-dimensional coordinate space, the position of a reference space in which the number of coordinate points is greater than a threshold and in which the number of bright points is greater than in the surrounding area thereof is extracted, and then, the group of bright points contained in the reference space at the extracted position is classified into a group that corresponds a first substance.

Subsequently, the processing unit 111 obtains the range of the nucleus in the three-dimensional space of each test cell. Specifically, the processing unit 111 causes the objective lens 17 to move in the optical axis direction of the image capturing unit 19, and obtains images at a plurality of different focus positions in the optical axis direction. At this time, the region in which fluorescence based on the third fluorescent dyes is detected corresponds to the nucleus, and the region in which fluorescence based on the third fluorescent dyes is not detected corresponds to a substance other than the nucleus, i.e., corresponds to cytoplasm. The processing unit 111 obtains the contour of the nucleus from the region in which fluorescence has been detected, for each of the obtained plurality of images. Then, on the basis of each focus position and the contour of the nucleus at that position, the processing unit 111 obtains the range of the nucleus in the three-dimensional space. Examples of the third fluorescent dye include a 7-AAD, DAPI, SYTOX-based fluorescent dye, a SYTO-based fluorescent dye, propidium iodide, and the like, in addition to Hoechst 33342 described above. Then, the processing unit 111 obtains, as the number of the first substances, the number of the groups contained in the range of the nuclei of the test cells.

Figure 17A:
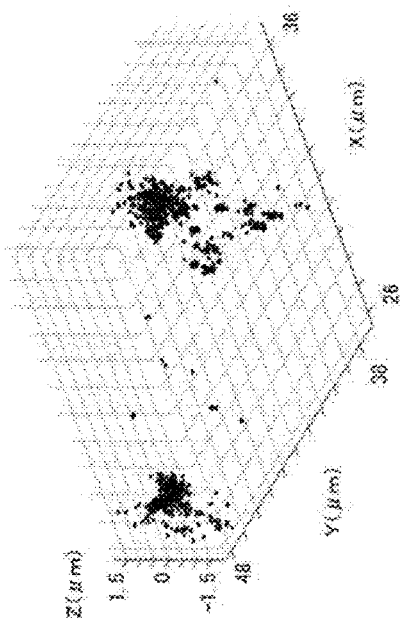
FIG. 17A is a diagram showing a three-dimensional super-resolution image according to Embodiment 3.
Figure 17B:
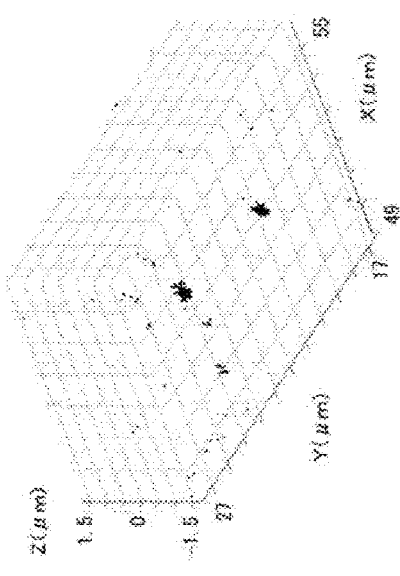
FIG. 17B is a diagram showing a three-dimensional super-resolution image according to Embodiment 3.
Figure 17C:
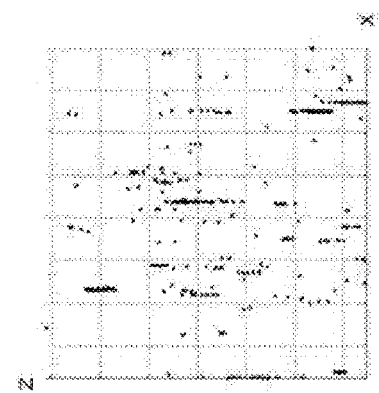
FIG. 17C is a diagram showing an image when a three-dimensional super-resolution image is viewed in a Z-axis direction according to Embodiment 3.
Figure 17D:
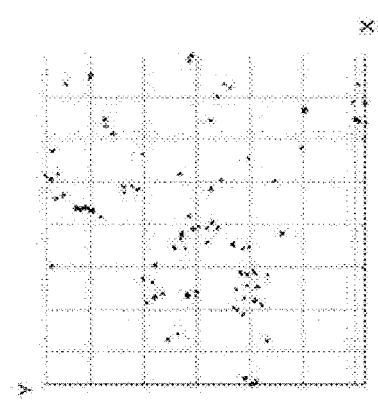
FIG. 17D is a diagram showing an image when a three-dimensional super-resolution image is viewed in a Y-axis direction according to Embodiment 3.

For example, the three-dimensional super-resolution image is obtained as shown in FIGS. 17A and 17B. In each figure, the X-Y plane is the two-dimensional plane at the image capture angle, and the Z-axis direction is the optical axis direction of the image capturing unit 19. FIGS. 17A and 17B are actually-obtained three-dimensional super-resolution images of samples whose results of determination regarding breast cancer are negative and positive, respectively. When the three-dimensional super-resolution images of FIGS. 17A and 17B are viewed in the Z-axis direction and the Y-axis direction, the images as shown in FIGS. 17C and 17D can be obtained, respectively.

Figure 18:
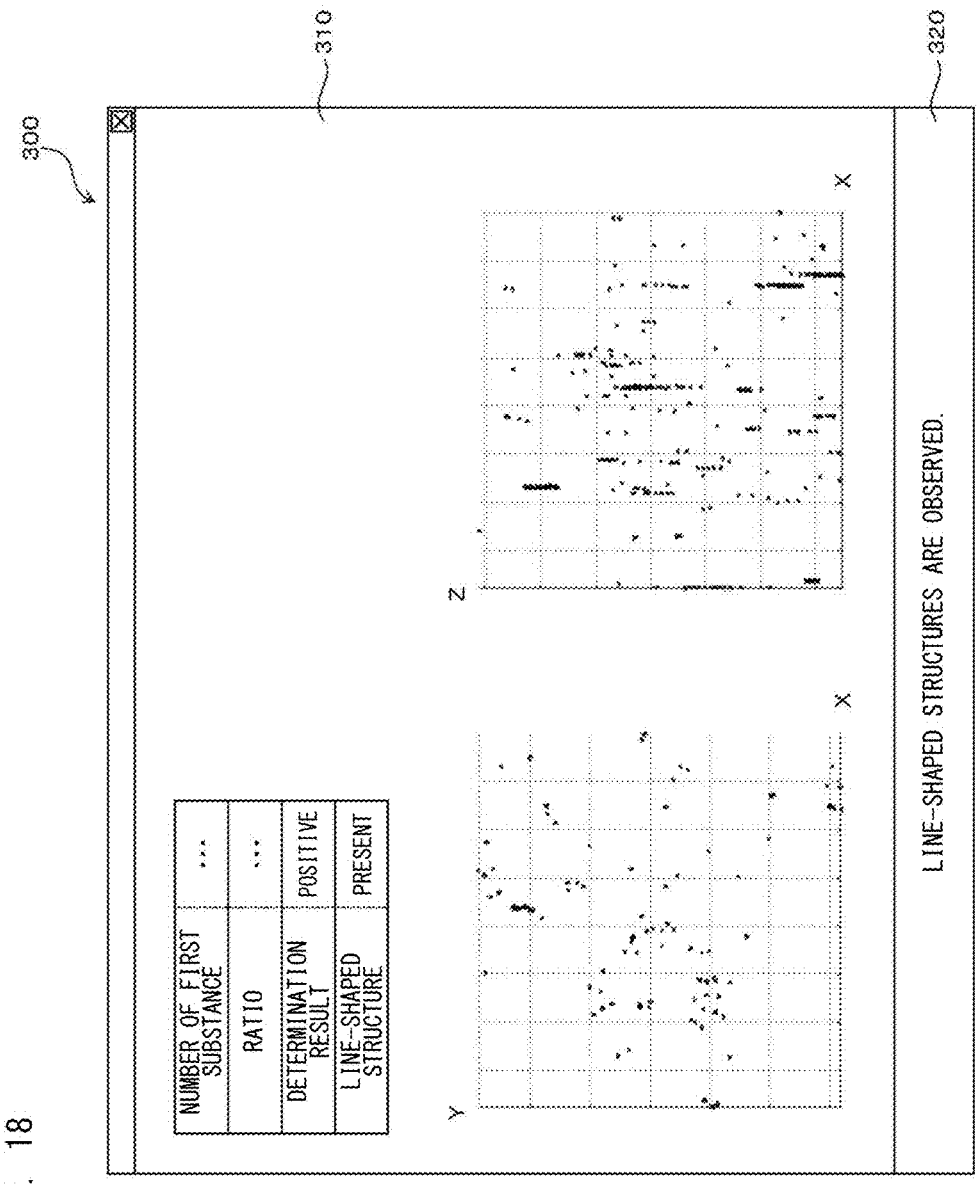
FIG. 18 is a diagram showing a configuration of a screen displayed on a display unit according to Embodiment 3.

When a three-dimensional super-resolution image is created, a screen 300 as shown in FIG. 18 is displayed on the display unit 120 in the display process. Similarly to the screen 200 shown in FIGS. 12A and 12B, the screen 300 includes a result region 310 and a comment region 320. In the result region 310, images obtained when a three-dimensional super-resolution image is viewed in the Z-axis direction and in the Y-axis direction are displayed. In the result region 310, three-dimensional super-resolution images as shown in FIGS. 17A and 17B may be displayed.

According to Embodiment 3, with respect to the first fluorescent dyes, a three-dimensional super-resolution image can be obtained that allows identification of the position in the optical axis direction of the image capturing unit 19 as well as the position on the two-dimensional plane at the image capture angle. Thus, bright points that are overlapped with one another on the two-dimensional plane can also be separated and extracted. Accordingly, the number of the first substances can be further accurately counted, and a more accurate determination result can be presented to the doctor or the like. In addition, by referring to the three-dimensional super-resolution image, the doctor or the like can also understand the distribution of the first substances in the optical axis direction, and thus, can perform disease condition judgement and therapeutic strategy decision more accurately.

The distance between the first substances and the distribution state of the first substances may be obtained on the basis of the three-dimensional super-resolution image. The three-dimensional super-resolution image allows more accurate understanding of the distance between the first substances and the distribution state of the first substances. Thus, disease condition judgement and therapeutic strategy decision can be more accurately performed. In addition, also with respect the second substances, a three-dimensional super-resolution image may be obtained, and on the basis of the obtained three-dimensional super-resolution image, the distance between the second substances and the distribution state of the second substances may be obtained. Also in this case, the distance between the second substances and the distribution state of the second substances can be more accurately understood. Thus, disease condition judgement and therapeutic strategy decision can be more accurately performed.

In Embodiments 1 to 3, the disease as the therapy target is breast cancer, and the first substance serving as therapeutic strategy judgement index is HER-2. However, not limited thereto, another disease may be set as the therapy target, and the first substance serving as the therapeutic strategy judgement index may be another substance in accordance with the target disease. The second substance may also be another substance in accordance with the target disease. In a case where the first substance is another substance, different from the embodiments described above, it could be assumed that the first substances are decreased than that in a normal state, depending on the disease condition. The approaches of Embodiments 1 to 3 can be also used in detection of decrease of the first substances as appropriate. Thus, similarly to the case where HER-2 is the target, decrease of the first substances can be accurately detected. In addition, also when the second substances increase or decrease depending on the disease condition, the approaches of Embodiments 1 to 3 can be similarly applied.

What is claimed is:

1. A cell analyzer comprising:
    a light source unit configured to apply light to a test cell of which a first substance is stained with a first fluorescent dye;
    an image capturing unit configured to capture an image of fluorescence caused by the light; and
    a processing unit configured to process the image obtained by the image capturing unit,
    wherein the processing unit is programmed to obtain a first image by performing an inactivation process of quenching the first fluorescent dye, an activation process of activating a part of the first fluorescent dye that have been quenched, and an image capturing process of capturing, by the image capturing unit, an image of the fluorescence by applying light from the light source unit to the test cells;
    wherein said processing unit is programmed to extract bright points based on the first fluorescent dye on the basis of the first image; and
    wherein said processing unit is programmed to classify the extracted bright points into groups each corresponding to one first substance, thereby to obtain the number of the first substances in the test cell on the basis of the number of the classified groups.

2. The cell analyzer of claim 1, wherein
    the processing unit further obtains information regarding a distribution state of the first substances.

3. The cell analyzer of claim 1, wherein
    the processing unit further obtains information regarding location of the first substances.

4. The cell analyzer of claim 1, wherein
    each first substance is a gene that changes in a specific manner in a cell with a specific disease or a protein that changes in a specific manner in a cell with a specific disease.

5. The cell analyzer of claim 1, wherein
    each first substance is a cancer marker gene or a cancer marker protein.

6. The cell analyzer of claim 1, wherein
    the light source unit applies light to a test cell containing the first substance stained with the first fluorescent dye; and second substance stained with a second fluorescent dye that are different from the first fluorescent dye, and
    the processing unit further obtains a number of the second substance on the basis of a captured image of fluorescence generated from the second fluorescent dye.

7. The cell analyzer of claim 6, wherein
    the processing unit further obtains information regarding location of the second substances.

8. The cell analyzer of claim 6, wherein
    the processing unit obtains a therapy index information on the basis of a ratio between the number of the first substances and the number of the second substances.

9. The cell analyzer of claim 8, wherein
    the processing unit determines presence/absence of change in the first substances on the basis of the ratio between the number of the first substances and the number of the second substances.

10. The cell analyzer of claim 6, wherein
the first substance is HER-2 gene contained in a nucleus of the test cell, and
the second substance is CEP17 contained in the nucleus of the test cell.

11. The cell analyzer of claim 6, wherein
the processing unit obtains a second image without performing an inactivation process of quenching the second fluorescent dye, and counts the number of the second substances in the test cell on the basis of the second image.

12. The cell analyzer of claim 6, wherein
the processing unit obtains a second image by performing an inactivation process of quenching the second fluorescent dye, an activation process of activating a part of the second fluorescent dye that have been quenched, and an image capturing process of capturing an image of the fluorescence by applying light from the light source unit to the test cell; and counts the number of the second substances in the test cell on the basis of the second image.

13. The cell analyzer of claim 6, wherein
the processing unit obtains the first image and a second image by performing the inactivation process of quenching the first fluorescent dye and an inactivation process of quenching the second fluorescent dye, an activation process of activating a part of the first fluorescent dye that have been quenched and a part of the second fluorescent dye that have been quenched, and an image capturing process of capturing an image of the fluorescence by applying light from the light source unit to the test cell; and counts the number of the second substances in the test cell on the basis of the second image.

14. The cell analyzer of claim 1, wherein
the processing unit
performs a first processing step in which, before the first image is obtained, a process of quenching and reactivating the first fluorescent dye is performed once, then the first image of the first fluorescent dyes is obtained, and a determination index indicating presence/absence of change in the first substances is obtained on the basis of the obtained first image;
when the change in the first substances obtained in the first processing step is negative, causes a display unit to display the determination index obtained in the first processing step, as therapy index information;
when the change in the first substances obtained in the first processing step is not negative, performs a second processing step in which
the first image is obtained by performing the inactivation process, the activation process, and the image capturing process, and
the number of the first substances is obtained by performing a process of extracting the bright points and classifying the bright points with respect to the obtained first image.

15. The cell analyzer of claim 1, wherein
the processing unit performs an activation process of activating the first fluorescent dye from a quenched state, by applying light having a predetermined wavelength.

16. The cell analyzer of claim 1, wherein
the processing unit further causes a display unit to display an image indicating a distribution state of the bright points of the first fluorescent dyes.

17. The cell analyzer of claim 1, wherein
the image capturing unit is configured to obtain, with respect to each first fluorescent dye, a captured image that allows identification of a position in an optical axis direction as well as a position on a two-dimensional plane at an image capture angle, and
the processing unit extracts bright points of a plurality of the first fluorescent dye on the basis of the positions on the two-dimensional plane and the positions in the optical axis direction, and classifies the extracted bright points into groups each corresponding to a first substance, thereby to obtain the number of the first substances.

18. The cell analyzer of claim 1, wherein
a nucleus of the test cell is stained by third fluorescent dyes, and
the processing unit identifies a region of the nucleus in the test cell on the basis of a captured image of fluorescence generated from the third fluorescent dye, and obtains the number of the first substances for each identified region.

19. A cell analyzer controlling method comprising:
obtaining a first image by performing
an inactivation process of quenching first fluorescent dye bound to one or more first substances in a test cell,
an activation process of activating a part of the first fluorescent dye that have been quenched, and
an image capturing process of capturing an image of fluorescence by applying light to the test cell;
extracting bright points based on the first fluorescent dye on the basis of the first image; and
classifying the extracted bright points into groups each corresponding to one first substance, thereby to obtain the number of the first substances in the test cell on the basis of the number of the classified groups.

20. A non-transitory computer-readable computer medium storing a program for causing a computer of a cell analyzer to perform operations, wherein said program is programmed to: obtain a first image by performing an inactivation process of quenching a first fluorescent dye, an activation process of activating a part of the first fluorescent dye that have been quenched, and an image capturing process of capturing an image of the fluorescence;
extract bright points based on the first fluorescent dye on the basis of the first image; and
classify the extracted bright points into groups each corresponding to one first substance, thereby to obtain the number of the first substances in a test cell on the basis of the number of the classified groups.

21. A cell analyzer comprising:
a light source configured to irradiate light onto a test cell of which a first substance is stained with a first fluorescent dye;
an imaging device configured to capture an image of the test cell; and
a processing unit programmed to:
repeatedly quench and activate the first fluorescent dye in the test cell;
cause the imaging device to capture a plurality of images of the test cell under an irradiation by the light source while quenching and activating;
extract one or more bright points in the images; and quantify a number of the first substance residing in the test cell based on the extracted bright points.

22. A cell analyzer comprising:

first and second light sources configured to irradiate light with different wavelengths onto a test cell of which a first substance is stained with a first fluorescent dye;

an imaging device configured to capture an image of the test cell; and a processor programmed to:

cause the first light source to irradiate light onto the test cell to activate the first fluorescent dye in the test cell;

cause the second light source to irradiate light onto the test cell to quench the first fluorescent dye in the test cell;

cause the imaging device to capture a plurality of images of the test cell in the course of quenching during the irradiation by the second light source;

merge the images; and quantify a number of the first substance residing in the test cell based on the merged image.

\* \* \* \* \*